(12) United States Patent
Yuen

(10) Patent No.: US 6,833,385 B2
(45) Date of Patent: Dec. 21, 2004

(54) 3-HETEROARYLALKYL SUBSTITUTED GABA ANALOGS

(75) Inventor: Po-Wai Yuen, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/741,116

(22) Filed: Dec. 19, 2003

(65) Prior Publication Data

US 2004/0127724 A1 Jul. 1, 2004

Related U.S. Application Data

(63) Continuation of application No. 09/979,344, filed as application No. PCT/US00/11397 on Apr. 28, 2000, now Pat. No. 6,710,190.
(60) Provisional application No. 60/136,491, filed on May 28, 1999.

(51) Int. Cl.[7] .................. C07D 333/10; A61K 31/381
(52) U.S. Cl. ......................... 514/438; 549/76
(58) Field of Search ............... 547/76; 514/438

(56) References Cited

U.S. PATENT DOCUMENTS

| | | | |
|---|---|---|---|
| 4,024,175 A | 5/1977 | Satzinger et al. | 260/468 |
| 4,087,544 A | 5/1978 | Satzinger et al. | 424/305 |

FOREIGN PATENT DOCUMENTS

| | | |
|---|---|---|
| EP | 0446097 | 2/1991 |
| EP | 2722192 | 7/1994 |
| JP | 119936 | 5/1996 |
| WO | 9913907 | 3/1999 |

OTHER PUBLICATIONS

Keenan et al., "Imidazole–5–acrylic Acids: Potent Nonpeptide Angiotensl II Receptor Antagonists Designed Using a Novel Peptide Pharmacophore Model", *Journal of Medicinal Chemistry*, American Chemical Society, vol. 35, No. 21, 1992, pp 3858–3872.

Floyd, "Prostaglandins and Congeners, 18, Synthesis of Cyclopentenolone Precursors to Prostaglandins from 2,5–Dihydro–2,5–dimethoxyfurans", *Journal of Organic Chemistry*, vol. 43, No. 9, 1978, pp 1641–1643.

Brown, et al., Isocytosine $H_2$–receptor histamine antagonist II. Synthesis and evaluation of biological activity at histamine $H_1$–and $H_2$–receptors of 5–(heterocyclyl) methylisocytosines, *European Journal of Medicinal Chemistry* vol. 24, 1989, pp 65–72.

Climent, et al., "Ba(OH)2 as Catalyst in Organic Reactions. 20. Structure–Catalytic Activity Relationship in the Wittig Reaction", *Journal of Organic Chemistry*, vol. 54, 1989, pp 3695–3701.

PCT International Search Report—PCT/US00/11397.

*Primary Examiner*—Golam M M Shameem
(74) *Attorney, Agent, or Firm*—Mehdi Ganjeizadeh

(57) ABSTRACT

The invention is a novel series of compounds which are useful in the treatment of epilepsy, faintness attacks, neurodegenerative disorders, depression, anxiety, panic, pain, neuropathological disorders, gastrointestinal disorders such as irritable bowel syndrome (IBS), and inflammation, especially arthritis. A pharmaceutical composition containing a compound of the invention as well as methods of preparing the compounds and novel intermediates useful in the preparation of the final compounds are included.

3 Claims, No Drawings

US 6,833,385 B2

3-HETEROARYLALKYL SUBSTITUTED GABA ANALOGS

This application is a Continuation of U.S. application Ser. No. 09/979,344, filed Nov. 21, 2001, now U.S. Pat. No. 6,710,190 which is a 371 filing of PCT/US00/11397 filed Apr. 28, 2000, which claims the benefit of U.S. Provisional Application 60/136,491 filed May 28, 1999, the entire contents of which applications are hereby incorporated herein by reference.

Compounds of formula:

$$H_2N-CH_2-\underset{\underset{(CH_2)_n}{\bigcirc}}{C}-CH_2-COOR_1$$

wherein $R_1$ is hydrogen or a lower alkyl radical and n is 4, 5, or 6 are known in U.S. Pat. No. 4,024,175 and its divisional U.S. Pat. No. 4,087,544. The uses disclosed are: protective effect against cramp induced by thiosemicarbazide; protective action against cardiazole cramp; the cerebral diseases, epilepsy, faintness attacks, hypokinesia, and cranial traumas; and improvement in cerebral functions. The compounds are useful in geriatric patients. The patents are hereby incorporated by reference.

SUMMARY OF THE INVENTION

The instant invention is a compound of Formula I and II

[Structure I]

and

[Structure II]

wherein A, X, Y, Z, W, and n are as described below.

The compounds of the invention and their pharmaceutically acceptable salts and the prodrugs of the compounds, are useful in the treatment of epilepsy, faintness attacks, hypokinesia, cranial disorders, neurodegenerative disorders, depression, anxiety, panic, pain, neuropathological disorders, gastrointestinal disorders such as irritable bowel syndrome (IBS), and inflammation, especially arthritis.

The invention is also a pharmaceutical composition of a compound of Formula I or II.

The invention also includes novel intermediates useful in the preparation of the final products.

DETAILED DESCRIPTION OF THE INVENTION

The compounds of the invention are those of Formula I and II:

[Structure I]

and

[Structure II]

or a pharmaceutically acceptable salt thereof wherein:

In Formula I, A is O, S, or NR wherein R is hydrogen, straight or branched alkyl of from 1 to 6 carbon atoms, cycloalkyl of from 3 to 8 carbon atoms, phenyl or benzyl;

In Formula II, A is N;

X, Y, Z and W are each independently hydrogen, straight or branched alkyl of from 1 to 6 carbon atoms;

cycloalkyl of from 3 to 8 carbon atoms, alkoxy, phenyl, benzyl, or halogen; and n is an integer of from 1 to 4.

Preferred compounds are those of Formula I and II wherein Formula I and II are:

[Structure I]

and

[Structure II]

Other preferred compounds are those of Formula I wherein A is oxygen.

Other preferred compounds are those of Formula I wherein A is sulfur.

Other preferred compounds are those of Formula I wherein A is NR.

When A is N, preferred compounds can also be those of Formula II.

More preferred compounds are selected from:

3-Aminomethyl-4-thiophen-2-yl-butyric acid;
3-Aminomethyl-4-thiophen-3-yl-butyric acid;
3-Aminomethyl-4-furan-2-yl-butyric acid;
3-Aminomethyl-4-furan-3-yl-butyric acid;
3-Aminomethyl-4-pyrrole-2-yl-butyric acid;
3-Aminomethyl-4-pyrrole-3-yl-butyric acid; and
3-Aminomethyl-4-pyrrole-1-yl-butyric acid;

The term lower alkyl is a straight or branched group of from 1 to 6 carbons including but not limited to methyl, ethyl, n-propyl, isopropyl, n-butyl, isobutyl, tert-butyl, pentyl, except as where otherwise stated.

The benzyl and phenyl groups may be unsubstituted or substituted by from 1 to 3 substituents selected from hydroxy, carboxy, carboalkoxy, halogen, $CF_3$, nitro, alkyl, and alkoxy. Preferred are alkyl.

Cycloalkyl is cyclic carbon group of from 3 to 8 atoms.

Alkoxy is a straight or branched group of from 1 to 4 carbons attached to the remainder of the molecule by an oxygen.

Halogen is chlorine, fluorine, bromine, or iodine.

The prodrugs of the compounds include, but are not limited to esters, amides, and carbamates.

Since amino acids are amphoteric, pharmacologically compatible salts of appropriate inorganic or organic acids, for example, hydrochloric, sulphuric, phosphoric, acetic, oxalic, lactic, citric, malic, salicylic, malonic, maleic, succinic, methanesulfonic acid, and ascorbic. Starting from corresponding hydroxides or carbonates, salts with alkali metals or alkaline earth metals, for example, sodium, potassium, magnesium, or calcium are formed. Salts with quaternary ammonium ions can also be prepared with, for example, the tetramethyl-ammonium ion. The carboxyl group of the amino acids can be esterified by known means.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

Methods and Materials

Animals

Male Sprague-Dawley rats (180–250 g) were obtained from Bantin and Kingman, (Hull, U.K.). Animals were housed in groups of 6 to 10 under a 12 hour light/dark cycle (lights on at 7 hours, 0 minutes) with food and water ad libitum.

Carrageenan-Induced Thermal Hyperalgesia in the Rat

Thermal hyperalgesia was assessed using the rat plantar test (Ugo Basile, Italy) following a modified method of Hargreaves, et al., 1988. Rats were habituated to the apparatus which consisted of three individual perspex boxes on an elevated glass table. A mobile radiant heat source located under the table was focused onto the desired paw and paw withdrawal latencies (PWL) recorded. PWL were taken 3 times for both hind paws of each animal, the mean of which represented baselines for right and left hind paws. At least 5 minutes were allowed between each PWL for an animal. The apparatus was calibrated to give a PWL of approximately 10 seconds. There was an automatic cutoff point of 20 seconds to prevent tissue damage. After baseline PWLs were determined, animals received an intraplantar injection of carrageenan (100 µL of 20 mg/mL) into the right hind paw. PWLs were reassessed following the same protocol as above 2-hour post-carrageenan (this time point represented the start of peak hyperalgesia) to ascertain that hyperalgesia had developed. Test compounds were administered orally (in a volume of 1 ml kg) at 2.5 hours after carrageenan. PWLs were reassessed at various times after drug administration.

A Model of Anticonvulsant Efficacy and Protocol for DBA2 Test: Prevention of Audiogenic Seizures in DBA/2 Mice Methods All procedures were carried out in compliance with the NIH Guide for the Care and Use of Laboratory Animals under a protocol approved by the Parke-Davis Animal Use Committee. Male DBA/2 mice, 3 to 4 weeks old, were obtained from Jackson Laboratories, Bar Harbour, Me. Immediately before anticonvulsant testing, mice were placed upon a wire mesh, 4 inches square suspended from a steel rod. The square was slowly inverted through 180 degrees and mice observed for 30 seconds. Any mouse falling from the wire mesh was scored as ataxic.

Mice were placed into an enclosed acrylic plastic chamber (21 cm height, approximately 30 cm diameter) with a high-frequency speaker (4 cm diameter) in the center of the top lid. An audio signal generator (Protek model B-810) was used to produce a continuous sinusoidal tone that was swept linearly in frequency between 8 kHz and 16 kHz once each 10 msec. The average sound pressure level (SPL) during stimulation was approximately 100 dB at the floor of the chamber. Mice were placed within the chamber and allowed to acclimatize for 1 minute. DBA/2 mice in the vehicle-treated group responded to the sound stimulus (applied until tonic extension occurred, or for a maximum of 60 seconds) with a characteristic seizure sequence consisting of wild running followed by clonic seizures, and later by tonic extension, and finally by respiratory arrest and death in 80% or more of the mice. In vehicle-treated mice, the entire sequence of seizures to respiratory arrest lasts approximately 15 to 20 seconds.

The incidence of all the seizure phases in the drug-treated and vehicle-treated mice was recorded, and the occurrence of tonic seizures were used for calculating anticonvulsant $ED_{50}$ values by probit analysis. Mice were used only once for testing at each dose point. Groups of DBA/2 mice (n=5–10 per dose) were tested for sound-induced seizure responses 2 hours (previously determined time of peak effect) after given drug orally. All drugs in the present study were dissolved in distilled water and given by oral gavage in a volume of 10 ml/kg of body weight compounds that are insoluble will be suspended in 1% carboxymethocellulose. Doses are expressed as weight of the active drug moiety.

Results

The dose-dependent suppression of sound-induced tonic seizures in DBA/2 mice was tested, and the corresponding $ED_{50}$ values are shown in Table 1.

The present results show that the compounds of the invention given orally cause dose-related anticonvulsant effects in a sound susceptible strain (DBA/2) of mice, confirming previous data showing anticonvulsant activity in other models of experimental epilepsy. The effective dosages of drugs in this model are lower than those in the maximal electroshock test, confirming that DBA/2 mice are a sensitive model for detecting anticonvulsant actions.

TABLE 1

| Structure | $\alpha_2\delta$ Assay IC$_{50}$ (µM) | Pain Model % MPE 1 h | Pain Model % MPE 2 h | DBA2 Mouse Model % Protect Time |
|---|---|---|---|---|
| (structure shown) | 0.421 | 61.6 | 24.9 | 0 (1 h) 20 (2 h) |

TABLE 1-continued

| Structure | α₂δ Assay IC$_{50}$ ($\mu$M) | Pain Model % MPE 1 h | 2 h | DBA2 Mouse Model % Protect Time |
|---|---|---|---|---|
| (thiophene-CH₂-CH(CH₂NH₂)-CH₂-COOH) | 0.831 | N/A | | 40 (1 h)<br>60 (2 h) |
| (thiophene-CH₂-CH(CH₂NH₂)-CH₂-COOH) | 2.67 | 31.9 | 18.1 | 20 (1 h)<br>40 (2 h) |

The radioligand binding assay using [³H]gabapentin and the α₂δ subunit derived from porcine brain tissue was used ("The Novel Anti-convulsant Drug, Gabapentin, Binds to the α₂δ Subunit of a Calcium Channel", Gee N. et al., *J. Biological Chemistry*, in press).

The compounds of the invention show good binding affinity to the α₂δ subunit. Gabapentin (Neurontin®) is about 0.10 to 0.12 $\mu$M in this assay. Since the compounds of the instant invention also bind to the subunit, they are expected to exhibit pharmacologic properties comparable to gabapentin. For example, as agents for convulsions, anxiety, and pain.

The compounds of the invention are related to Neurontin®, a marketed drug effective in the treatment of epilepsy. Neurontin® is 1-(aminomethyl)-cyclohexaneacetic acid of structural formula:

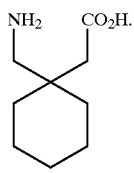

The compounds of the invention are also expected to be useful in the treatment of epilepsy.

The present invention also relates to therapeutic use of the compounds of the mimetic as agents for neurodegenerative disorders.

Such neurodegenerative disorders are, for example, Alzheimer's disease, Huntington's disease, Parkinson's disease, and Amyotrophic Lateral Sclerosis.

The present invention also covers treating neurodegenerative disorders termed acute brain injury. These include but are not limited to: stroke, head trauma, and asphyxia.

Stroke refers to a cerebral vascular disease and may also be referred to as a cerebral vascular incident (CVA) and includes acute thromboembolic stroke. Stroke includes both focal and global ischemia. Also, included are transient cerebral ischemic attacks and other cerebral vascular problems accompanied by cerebral ischemia such as in a patient undergoing carotid endarterectomy specifically or other cerebrovascular or vascular surgical procedures in general, or diagnostic vascular procedures including cerebral angiography and the like.

Other incidents are head trauma, spinal cord trauma, or injury from general anoxia, hypoxia, hypoglycemia, hypotension as well as similar injuries seen during procedures from embole, hyperfusion, and hypoxia.

The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

The compounds of the invention are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

GABA is an inhibitory neurotransmitter with the central nervous system. Within the general context of inhibition, it seems that GABA-mimetics will decrease or inhibit cerebral function and will therefore slow function and decrease mood leading to depression.

The compounds of the instant invention may produce an anticonvulsant effect through the increase of newly created GABA at the synaptic junction. If gabapentin does indeed increase GABA levels or the effectiveness of GABA at the synaptic junction, then it could be classified as a GABA-mimetic and might decrease or inhibit cerebral function and might, therefore, slow function and decrease mood leading to depression.

The fact that a GABA agonist or GABA-mimetic might work just the opposite way by increasing mood and thus, be an antidepressant, is a new concept, different from the prevailing opinion of GABA activity heretofore.

The compounds of the instant invention are also expected to be useful in the treatment of anxiety and of panic as demonstrated by means of standard pharmacological procedures.

Carrageenin-Induced Hyperalgesia, Another Method

Nociceptive pressure thresholds were measured in the rat paw pressure test using an analgesymeter (Randall-Sellitto Method: Randall L. O., Sellitto J. J., A method for measurement of analgesic activity on inflamed tissue. *Arch. Int. Pharmacodyn.*, 1957;4:409–419). Male Sprague-Dawley rats (70–90 g) were trained on this apparatus before the test day. Pressure was gradually applied to the hind paw of each rat and nociceptive thresholds were determined as the pressure (g) required to elicit paw withdrawal. A cutoff point of 250 g was used to prevent any tissue damage to the paw. On the test day, two to three baseline measurements were taken before animals were administered 100 $\mu$L of 2% carrageenin by intraplantar injection into the right hind paw. Nociceptive thresholds were taken again 3 hours after carrageenin to establish that animals were exhibiting hyperalgesia. Animals were dosed with either gabapentin (3–300 mg/kg, s.c.), morphine (3 mg/kg, s.c.), or saline at 3.5 hours after carrageenin and nociceptive thresholds were examined at 4, 4.5, and 5 hours post-carrageenin.

Semicarbazide-Induced Tonic Seizures

Tonic seizures in mice are induced by subcutaneous administration of semicarbazide (750 mg/kg). The latency to the tonic extension of forepaws is noted. Any mice not convulsing within 2.0 hours after semicarbazide are considered protected and given a maximum latency score of 120 minutes.

Animals

Male Hooded Lister rats (200–250 g) are obtained from Interfauna (Huntingdon, UK) and male TO mice (20–25 g) are obtained from Bantin and Kingman (Hull, UK). Both rodent species are housed in groups of six. Ten Common Marmosets (Callithrix Jacchus) weighing between 280 and 360 g, bred at Manchester University Medical School (Manchester, UK) are housed in pairs. All animals are housed under a 12-hour light/dark cycle (lights on at 07.00 hour) and with food and water ad libitum.

Drug Administration

Drugs are administered either intraperitoneally (IP) or subcutaneously (SC) 40 minutes before the test in a volume of 1 ml/kg for rats and marmosets and 10 ml/kg for mice.

Mouse Light/Dark Box

The apparatus is an open-topped box, 45 cm long, 27 cm wide, and 27 cm high, divided into a small (⅔) and a large (⅗) area by a partition that extended 20 cm above the walls (Costall B., et al., Exploration of mice in a black and white box: validation as a model of anxiety. *Pharmacol. Biochem. Behav.*, 1989;32:777–785).

There is a 7.5×7.5 cm opening in the center of the partition at floor level. The small compartment is painted black and the large compartment white. The white compartment is illuminated by a 60-W tungsten bulb. The laboratory is illuminated by red light. Each mouse is tested by placing it in the center of the white area and allowing it to explore the novel environment for 5 minutes. The time spent in the illuminated side is measured (Kilfoil T., et al., Effects of anxiolytic and anxiogenic drugs on exploratory activity in a simple model of anxiety in mice. *Neuropharmacol.*, 1989;28:901–905).

Rat Elevated X-Maze

A standard elevated X-maze (Handley S. L., et al., Effects of alpha-adrenoceptor agonists and antagonists in a maze-exploration model of 'fear'-motivated behavior. *Naunyn-Schiedeberg's Arch. Pharmacol.*, 1984;327: 1–5) was automated as previously described (Field, et al., Automation of the rat elevated X-maze test of anxiety. *Br. J. Pharmacol.*, 1991;102(Suppl):304P). The animals are placed on the center of the X-maze facing one of the open arms. For determining anxiolytic effects the entries and time spent on the end half sections of the open arms is measured during the 5-minute test period (Costall, et al., Use of the elevated plus maze to assess anxiolytic potential in the rat. *Br. J. Pharmacol.*, 1989;96(Suppl):312P).

Marmoset Human Threat Test

The total number of body postures exhibited by the animal towards the threat stimulus (a human standing approximately 0.5 m away from the marmoset cage and staring into the eyes of the marmoset) is recorded during the 2-minute test period. The body postures scored are slit stares, tail postures, scent marking of the cage/perches, piloerection, retreats, and arching of the back. Each animal is exposed to the threat stimulus twice on the test day before and after drug treatment. The difference between the two scores is analyzed using one-way analysis of variance followed by Dunnett's t-test. All drug treatments are carried out SC at least 2 hours after the first (control) threat. The pretreatment time for each compound is 40 minutes.

Rat Conflict Test

Rats are trained to press levers for food reward in operant chambers. The schedule consists of alternations of four 4-minute unpunished periods on variable interval of 30 seconds signaled by chamber lights on and three 3-minute punished periods on fixed ratio 5 (by footshock concomitant to food delivery) signaled by chamber lights off. The degree of footshock is adjusted for each rat to obtain approximately 80% to 90% suppression of responding in comparison with unpunished responding. Rats receive saline vehicle on training days.

The compounds of the instant invention are also expected to be useful in the treatment of pain and phobic disorders (*Am. J. Pain Manag.*, 1995;5:7–9).

The compounds of the instant invention are also expected to be useful in treating the symptoms of manic, acute or chronic, single upside, or recurring. They are also expected to be useful in treating and/or preventing bipolar disorder (U.S. Pat. No. 5,510,381).

Models of Irritable Bowel Syndrome

TNBS-Induced Chronic Visceral Allodynia in Rats

Injections of trinitrobenzene sulfonic (TNBS) into the colon have been found to induce chronic colitis. In human, digestive disorders are often associated with visceral pain. In these pathologies, the visceral pain threshold is decreased indicating a visceral hypersensitivity. Consequently, this study was designed to evaluate the effect of injection of TNBS into the colon on visceral pain threshold in a experimental model of colonic distension.

Materials and Methods

Animals and Surgery

Male Sprague-Dawley rats (Janvier, Le Genest-St-Ilse, France) weighing 340–400 g are used. The animals are housed 3 per cage in a regulated environment (20±1° C., 50±5% humidity, with light 8:00 am to 8:00 pm). Under anesthesia (ketamine 80 mg/kg i.p; acepromazin 12 mg/kg ip), the injection of TNBS (50 mg/kg) or saline (1.5 mL/kg) is performed into the proximal colon (1 cm from the cecum). After the surgery, animals are individually housed in polypropylene cages and kept in a regulated environment (20±1° C., 50±5% humidity, with light 8:00 AM to 8:00 PM) during 7 days.

Experimental Procedure

At Day 7 after TNBS administration, a balloon (5–6 cm length) is inserted by anus and kept in position (tip of balloon 5 cm from the anus) by taping the catheter to the base of the tail. The balloon is progressively inflated by step of 5 mm Hg, from 0 to 75 mm Hg, each step of inflation lasting 30 seconds. Each cycle of colonic distension is controlled by a standard barostat (ABS, St-Dié, France). The threshold corresponds to the pressure which produced the first abdominal contraction and the cycle of distension is then discontinued. The colonic threshold (pressure expressed in mm Hg) is determined after performance of four cycles of distension on the same animal.

Determination of the Activity of the Compound

Data is analyzed by comparing test compound-treated group with TNBS-treated group and control group. Mean and sem are calculated for each group. The antiallodynic activity of the compound is calculated as follows:

Activity (%)=(group $C$–group $T$)/(group $A$–group $T$)

Group C: mean of the colonic threshold in the control group

Group T: mean of the colonic threshold in the TNBS-treated group

Group A: mean of the colonic threshold in the test compound-treated group

Statistical Analysis

Statistical significance between each group was determined by using a one-way ANOVA followed by Student's unpaired t-test. Differences were considered statistically significant at $p<0.05$.

Compounds

TNBS is dissolved in EtOH 30% and injected under a volume of 0.5 mL/rat. TNBS is purchased from Fluka.

Oral administration of the test compound or its vehicle is performed 1 hour before the colonic distension cycle.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or II or a corresponding pharmaceutically acceptable salt of a compound of Formula I or II.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted, and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

General Synthetic Routes

Synthesis of Ester 1,
Starting Material for Generic Structure I

1

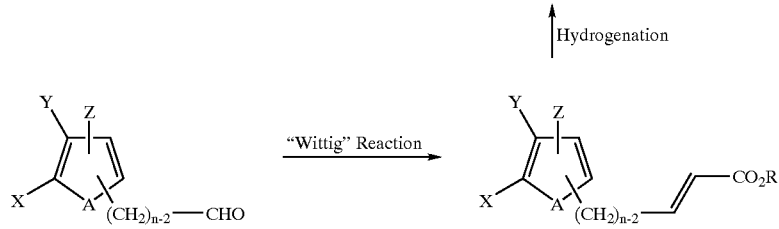

The ester 1 can be prepared by heating to reflux of the corresponding acid in a solvent such as ethanol and the like in the presence of a catalytic amount of mineral acid such as hydrochloric acid. It can also be prepared from the acid with an appropriate chloroformate in the presence of DMAP and a base such as triethylamine. Alternatively, the ester can also be prepared from the corresponding aldehyde via a "Wittig-like" reaction followed by hydrogenation of the double bond by catalytic hydrogenation according to methods described within the literature.

base, such as lithium diisopropylamide, in a solvent such as THF. The diester 2 can be selectively converted to the monoester 3 by saponification with an aqueous base, preferably lithium hydroxide. The acid 3 can be reduced to the alcohol 4 according to published literature procedures. The alcohol 4 can be converted to the azide 5 via a 2-step procedure involving first conversion of the alcohol into its tosylate or mesylate and then followed by treatment with excess sodium azide. The azide 5 can be converted to the GABA analog by another 2-step reaction sequence. Reduc- Synthesis of Compounds of Generic Structure I by Method A

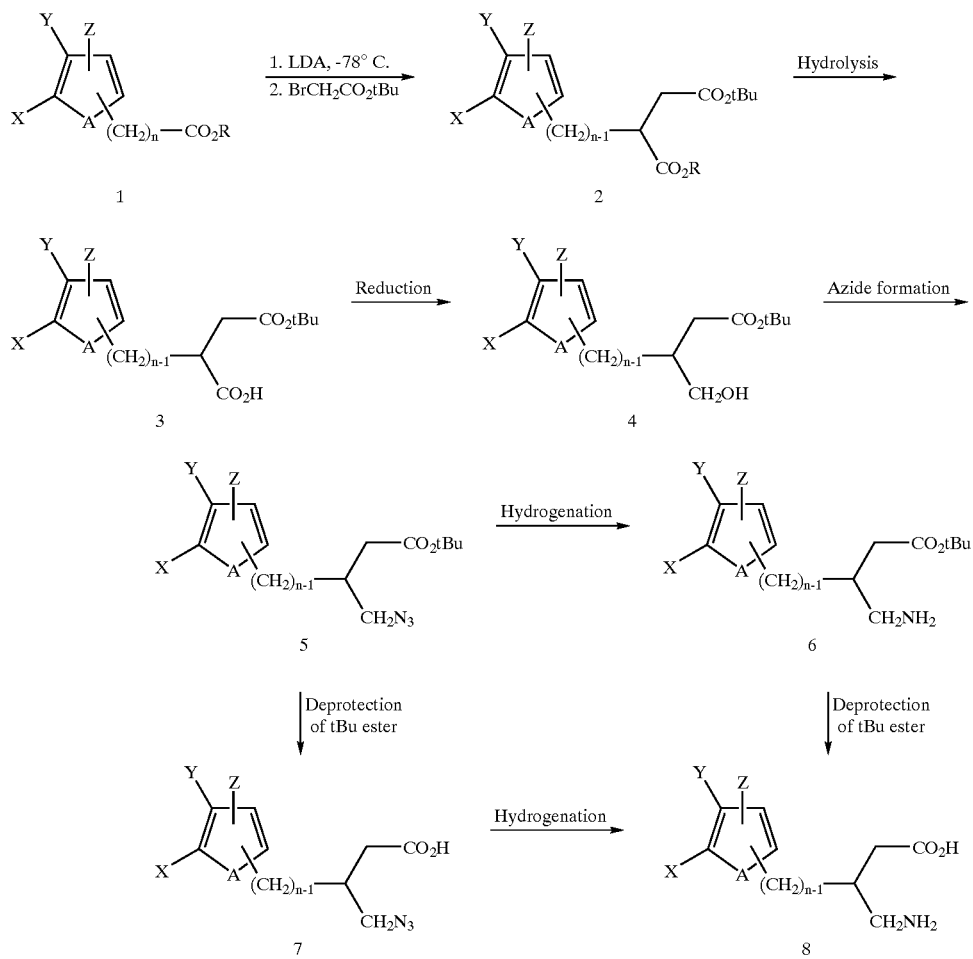

Diester of structure 2 can be prepared from the ester 1 by alkylation with t-butyl bromoacetate in the presence of a tion of the azide group to an amine-and then deprotection of the t-butyl ester to the acid 8 produced the desired GABA analog. Alternatively, the t-butyl ester can be deprotected first before the reduction of the azide. The sequence of reaction also gave the required amino acids.

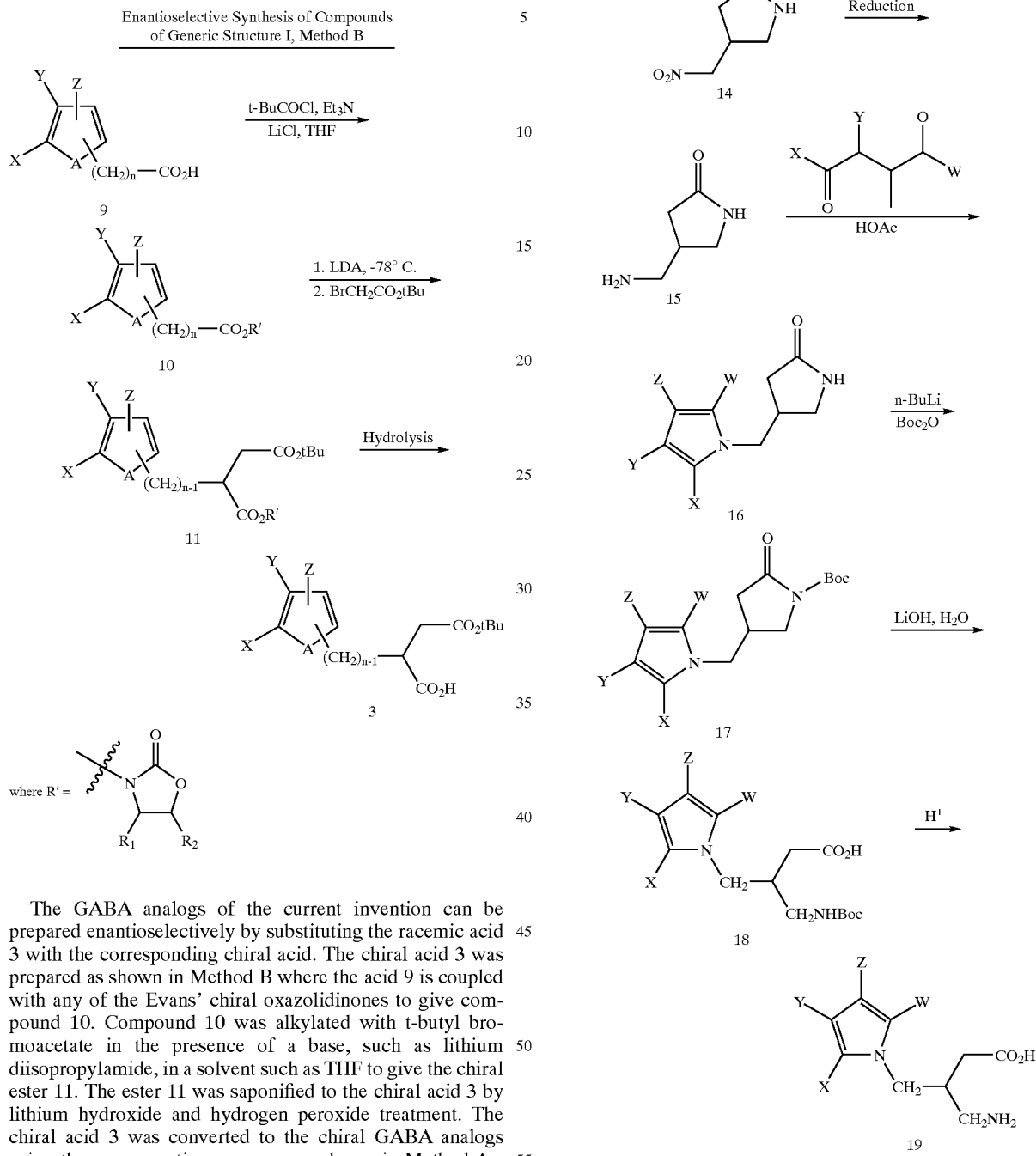

The GABA analogs of the current invention can be prepared enantioselectively by substituting the racemic acid 3 with the corresponding chiral acid. The chiral acid 3 was prepared as shown in Method B where the acid 9 is coupled with any of the Evans' chiral oxazolidinones to give compound 10. Compound 10 was alkylated with t-butyl bromoacetate in the presence of a base, such as lithium diisopropylamide, in a solvent such as THF to give the chiral ester 11. The ester 11 was saponified to the chiral acid 3 by lithium hydroxide and hydrogen peroxide treatment. The chiral acid 3 was converted to the chiral GABA analogs using the same reaction sequence as shown in Method A.

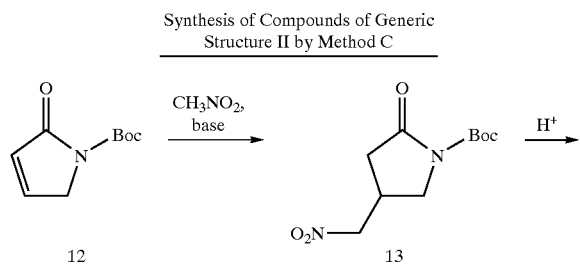

Method C can be used to prepare some of the GABA analogs of generic structure II in the current invention. The key intermediate 15 can be prepared from compound 12 via a 3-step Michael addition, Boc deprotection and reduction sequence. The amino lactam 15 can be reacted with an appropriately substituted carbonyl compound in the presence of an acid, preferably acetic acid to give the pyrrole derivative 16. Reprotection of the lactam 16 as its Boc analog followed by lithium hydroxide saponification will give the acid 18. The Boc protecting group can be removed by acid treatment to give the desired GABA analog 19.

Synthesis of Compounds of Generic Structure II by Method D

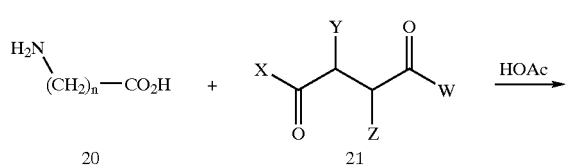

20    21

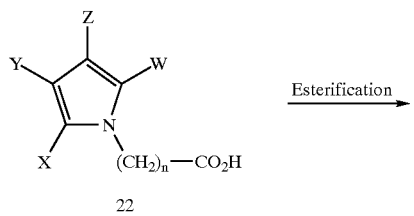

22

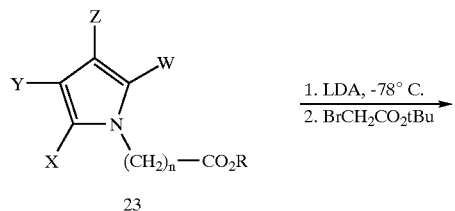

23

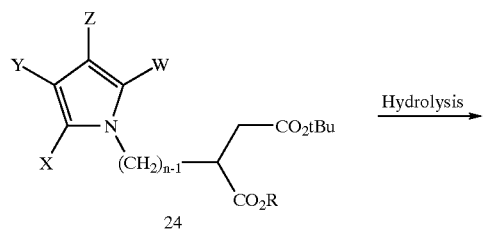

24

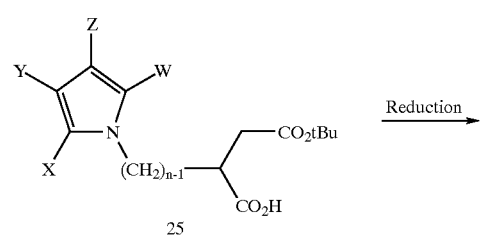

25

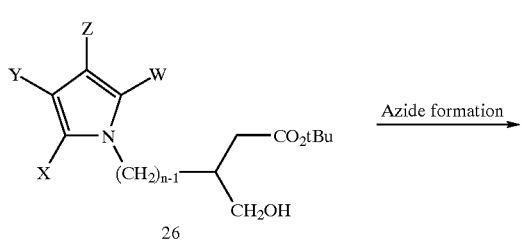

26

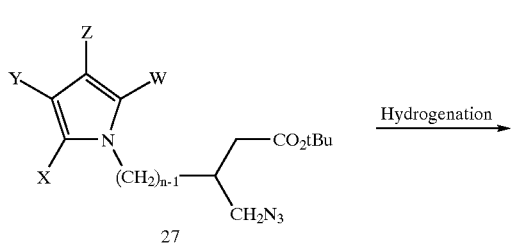

27

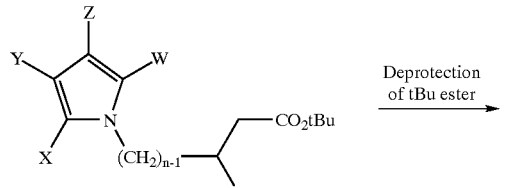

27

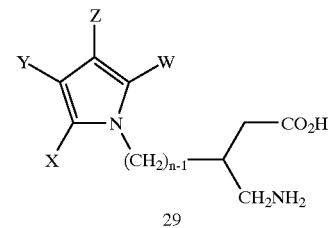

29

The acid 22 can be prepared by treating the amino acid 20 with an approximately substituted carbonyl compound 21 in the presence of an acid, preferably acetic acid. The ester 23 can be prepared by heating to reflux of the corresponding acid in a solvent such as ethanol and the like in the presence of a catalytic amount of mineral acid such as hydrochloric acid. It can also be prepared from the acid with an appropriate chloroformate in the presence of DMAP and a base such as triethylamine according to methods described within the literature. Diester of structure 24 can be prepared from the ester 23 by alkylation with t-butyl bromoacetate in the presence of a base, such as lithium diisopropylamide, in a solvent such as THF. The diester 24 can be selectively converted to the monoester 25 by saponification with an aqueous base, preferably lithium hydroxide. The acid 25 can be reduced to the alcohol 26 according to published literature procedures. The alcohol 26 can be converted to the azide 27 via a 2-step procedure involving first conversion of the alcohol into its tosylate or mesylate and then followed by treatment with excess sodium azide. The azide 27 can be converted to the GABA analog by another 2-step reaction sequence. Reduction of the azide group to an amine and then deprotection of the t-butyl ester to the acid 29 produced the desired GABA analog.

Enantioselective Synthesis of Compounds of Generic Structure II by Method E

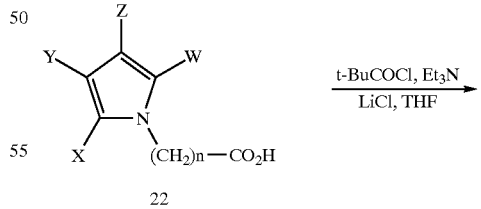

22

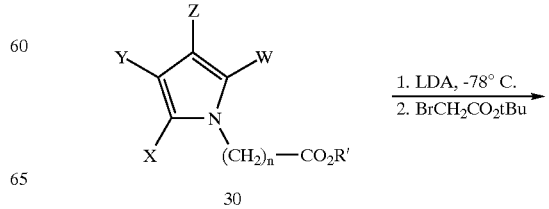

30

-continued

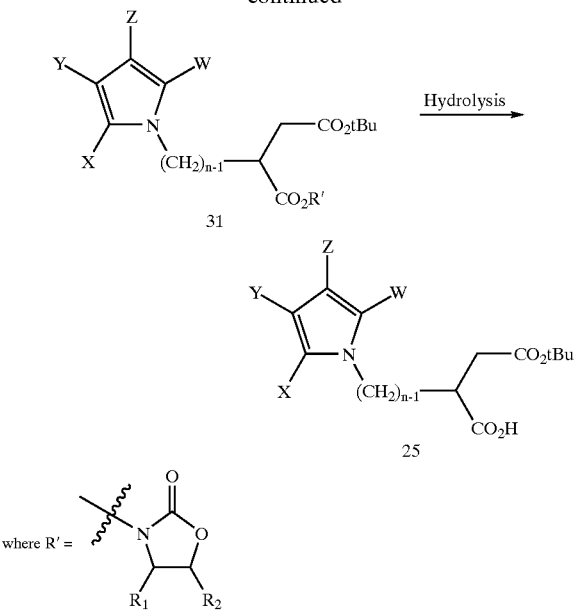

The GABA analogs of generic structure II in the current invention can be prepared enantioselectively by substituting the racemic acid 25 with the corresponding chiral acid. The chiral acid 3 was prepared as shown in Method E where the acid 22 is coupled with any of the Evans' chiral oxazolidinones to give compound 30. Compound 30 was alkylated with t-butyl bromoacetate in the presence of a base, such as lithium diisopropylamide, in a solvent such as THF to give the chiral ester 31. The ester 31 was saponified to the chiral acid 25 by lithium hydroxide and hydrogen peroxide treatment. The chiral acid 25 was converted to the chiral GABA analogs using the same reaction sequence as shown in Method D.

The following examples are illustrative of methods of preparation for the final products and intermediates of the invention, they are not intended to limit the scope.

EXAMPLE 1

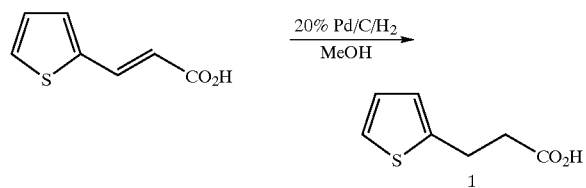

3-Thiophen-2-yl-propionic Acid 3-(2-Thienyl)acrylic acid (5.00 g, 32.43 mmol) was combined with 20% Pd/C (0.20 g) and methanol (150 mL) and stirred under a hydrogen atmosphere (1 atm) for 5 hours. Fresh catalyst (0.10 g) was added, and the reaction stirred another 6.5 hours under a hydrogen atmosphere (1 atm). The catalyst was filtered and washed with EtOAc (3×40 mL). The filtrate was concentrated to give the title compound 1 as a brown oil that crystallized upon standing (5.27 g, 100%).

$^1$H NMR (400 MHz, CDCl$_3$) δ 7.10 (d, 1H, J=5.13 Hz), 6.89 (m, 1H), 6.80 (d, 1H, J=2.20 Hz), 3.14 (t, 2H, J=7.57 Hz), 2.71 (t, 2H, J=7.57 Hz). MS (APCI) m/z 155 (M$^-$–1).

EXAMPLE 2

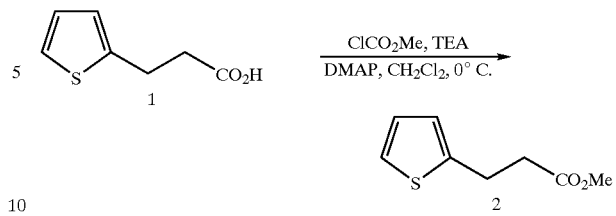

3-Thiophen-2-yl-propionic Acid Methyl Ester

Compound 1 (5.00 g, 32.01 mmol) was dissolved in anhydrous CH$_2$Cl$_2$ (100 mL) and cooled in an ice bath while stirring under N$_2$. Triethyl amine (4.95 mL, 35.53 mmol) was added, and the reaction stirred for 5 minutes. Methyl chloroformate (2.48 mL, 32.05 mmol) was added, the reaction stirred for 5 minutes, and DMAP (0.38 g, 3.11 mmol) added. The reaction was stirred at 0° C. for 30 minutes, and then diluted with CH$_2$Cl$_2$ (200 mL). The organics were washed with saturated NaHCO$_3$ (100 mL), 0.1 M HCl (100 mL), brine (100 mL), and dried over MgSO$_4$. The crude material was chromatographed on SiO$_2$ eluting with 7% EtOAc/hexanes to give the title compound 2 (3.976 g, 73%) as a colorless oil).

$^1$H NMR (400 MHz, CDCl$_3$) δ 7.10 (dd, 1H, J=4.64, 0.98 Hz), 6.88 (t, 1H, J=4.27 Hz), 6.78 (dd, 1H, J=2.20, 0.98 Hz), 3.66 (s, 3H), 3.13 (t, 2H, J=7.57 Hz), 2.66 (t, 2H, J=7.57 Hz). MS (APCI) m/z 171 (M$^+$+1).

EXAMPLE 3

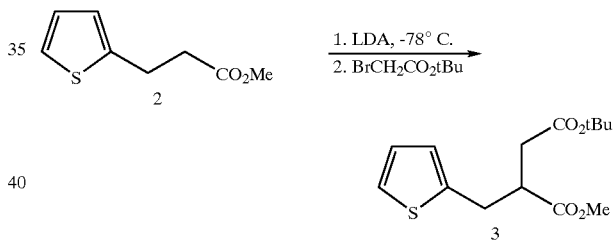

2-Thiophen-2-ylmethyl-succinic Acid Dimethyl Ester

Diisopropyl amine (2.1 mL, 15.0 mmol) was dissolved in anhydrous THF (35 mL) and cooled to −78° C. nBuLi (8.81 mL, 1.6 M, 14.1 mmol) was added, and the reaction stirred for 30 minutes at −78° C. Compound 2 (2.00 g, 11.75 mmol) was diluted up in THF (5 mL) and added dropwise to the LDA solution. After addition, the reaction was stirred for 30 minutes at −78° C. t-Butyl bromoacetate (2.60 mL, 17.6 mmol) was dissolved in THF (25 mL) and cooled to −78° C. The LDA solution was added via cannula to the t-butylbromo acetate solution, and the reaction stirred at −78° C. for 90 minutes. The reaction was quenched with saturate NaH$_2$PO$_4$. The layers were separated, and the aqueous layer extracted with EtOAc (3×20 mL). The combined organics were dried over MgSO$_4$, filtered and concentrated. The crude oil was chromatographed on SiO$_2$ eluting with 7% EtOAc/hexanes to give the title compound 3 (1.811 g, 54%) as an oil.

$^1$H NMR (400 MHz, CDCl$_3$) δ 7.11 (d, 1H, J=5.13 Hz), 6.88 (m, 1H), 6.76 (d, 1H, J=2.93 Hz), 3.66 (s, 3H), 3.18 (m, 1H), 3.06–2.99 (m, 2H), 2.56 (dd, 1J=16.60, 8.55 Hz), 2.37 (dd, 1H, J=16.60, 4.64 Hz), 1.39 (s, 9H). MS (APCI) m/z 211 (M$^+$–73, OtBu).

EXAMPLE 4

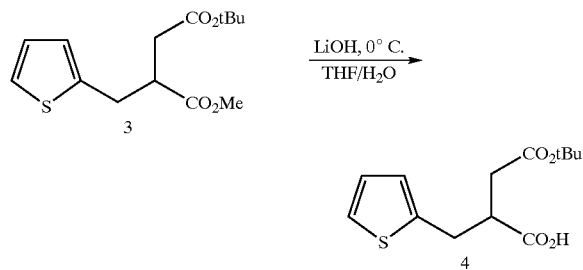

2-Thiophen-2-ylmethyl-succinic Acid 4-tert-butyl Ester

Compound 3 (1.80 g, 6.33 mmol) was dissolved in THF (20 mL) and cooled in an ice bath. LiOH (9.49 mL, 1N, 9.49 mmol) was added, followed by iPrOH (3 mL). The reaction was stirred at room temperature for 18 hours. The solvent was rotovapped off, and the residue diluted with water (50 mL). The water was extracted with ether (2×20 mL), acidified with saturated $NaH_2PO_4$, and extracted with EtOAc (3×50 mL). The combined organics were dried over $MgSO_4$, filtered, and concentrated to give the title compound 4 (1.611 g, 94%) as an oil that crystallized upon standing.

$^1$H NMR (400 MHz, $CDCl_3$) δ 7.12 (d, 1H, J=4.88 Hz), 6.89 (dd, 1H, J=4.88, 3.42 Hz), 6.80 (d, 1H, J=2.69 Hz), 3.24 (m, 1H), 3.09–3.02 (m, 2H), 2.56 (dd, 1H, J=16.60, 8.55 Hz), 2.40 (dd, 1H, J=16.60, 4.64 Hz), 1.39 (s, 9H). MS (APCI) m/z 269 (M$^-$−1). Analysis calculated for $C_{13}H_{18}O_4S$: C, 57.76; H, 6.78; S, 11.74. Found: C, 57.85; H, 6.78; S, 11.74.

EXAMPLE 5

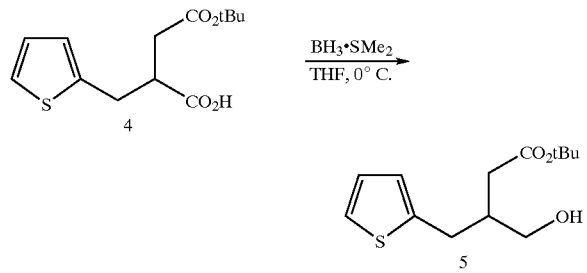

3-Hydroxymethyl-4-thiophen-2-yl-butyric Acid Tert-Butyl Ester

Compound 4 (1.576 g, 5.83 mmol) was dissolved in anhydrous THF (60 mL) and cooled in an ice bath. Borane dimethyl sulfide complex (2.91 mL, 29.1 mmol) was added dropwise, and the reaction stirred at 0° C. for 15 minutes, then at room temperature for 18 hours. The reaction was cooled again in an ice bath and quenched with methanol (25 mL) added dropwise. The solvent was then concentrated and the crude oil chromatographed on silica eluting with 25% EtOAc/hexanes to give the title compound 5 (1.05 g, 70%).

$^1$H NMR (400 MHz, $CDCl_3$) δ 7.11 (d, 1H, J=5.1 Hz), 6.89 (dd, 1H, J=5.0, 3.5 Hz), 6.78 (d, 1H, J=2.69 Hz), 3.62 (m, 1H), 3.53 (m, 1H), 2.90–2.83 (m, 2H), 2.29 (s, 3H), 1.90 (t, 1H, J=5.61 Hz), 1.42 (s, 9H). MS (APCI) m/z 183 (M$^+$−73, -OtBu).

EXAMPLE 6

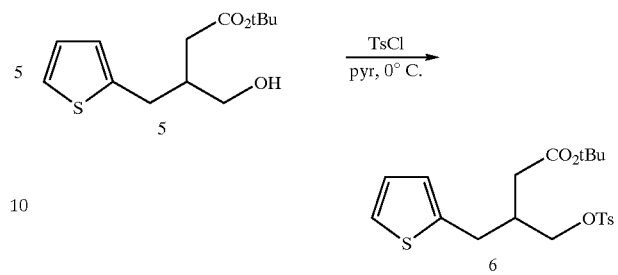

4-Thiophen-2-yl-3-(toluene-4-sulfonyloxymethyl)-butyric Acid Tert-Butyl Ester Compound 5 (1.032 g, 4.03 mmol) was dissolved in anhydrous pyridine (8 mL) and cooled to 0° C. Tosyl chloride (1.075 g, 5.64 mmol) was added, and the reaction stirred at 0° C. for 1 hour. The reaction was then placed in a freezer overnight. The reaction was then diluted with EtOAc (75 mL). The solids were filtered and washed with EtOAc (30 mL). The filtrate was then washed with water (30 mL), 1N HCl (30 mL), and then brine (2×30 mL). The organics were dried over $MgSO_4$, filtered, and concentrated to give an oil. This was chromatographed on silica eluting with 15% EtOAc/hexanes to give the title compound 6 (1.486 g, 90%).

$^1$H NMR (400 MHz, $CDCl_3$) δ 7.73 (d, 2H, J=8.3 Hz), 7.29 (d, 2H, J=8.1 Hz), 7.08 (m, 1H), 6.83 (dd, 1H, J=5.0, 3.41 Hz), 6.65 (d, 1H, J=2.44 Hz), 3.98 (dd, 1H, J=9.64, 4.74 Hz), 3.92 (dd, 1H, J=9.52, 4.64 Hz), 2.83 (m, 2H), 2.41 (s, 3H), 2.37 (m, 1H), 2.24 (m, 2H), 1.37 (s, 9H). MS (APCI) m/z 337 (M$^+$−73, -OtBu).

EXAMPLE 7

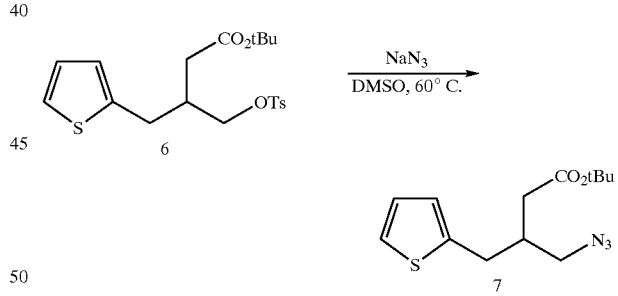

3-Azidomethyl-4-thiophen-2-yl-butyric Acid Tert-Butyl Ester

Compound 6 (1.486 g, 3.62 mmol), $NaN_3$ (0.54 g, 8.32 mmol), and DMSO (18 mL) were combined and heated to 60° C. for 17 hours. Water (50 mL) was added to the reaction and extracted with hexanes (4×30 mL). The combined organics were dried over $MgSO_4$, filtered, and concentrated to give the title compound 7 (0.965 g, 95%) as an oil.

$^1$H NMR (400 MHz, $CDCl_3$) δ 7.12 (dd, 1H, J=5.13, 1.22 Hz), 6.90 (dd, 1H, J=5.00, 3.54 Hz), 6.78 (m, 1H), 3.34 (dd, 1H, J=12.2, 5.1 Hz), 3.29 (dd, 1H, J=12.3, 5.2 Hz), 2.91–2.83 (m, 2H), 2.35–2.30 (m, 1H), 2.29–2.23 (m, 2H), 1.42 (s, 9H).

EXAMPLE 8

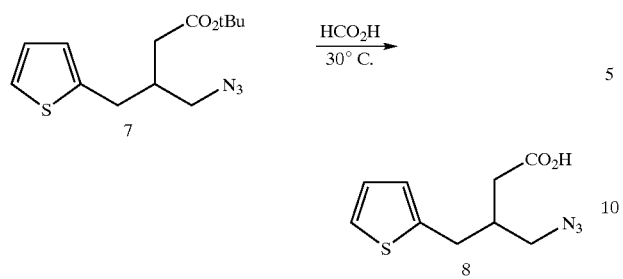

3-Azidomethyl-4-thiophen-2-yl-butyric Acid

Compound 7 (0.950 g, 3.38 mmol) was dissolved in formic acid (8 mL, 88%) and heated to 30° C. for 2 hours. The reaction was cooled and the formic acid removed. The residue was diluted with water and extracted with hexanes/ether, followed by ether (3×40 mL). The combined organics were dried over MgSO$_4$, filtered and concentrated to give the title compound 8 (0.738 g, 97%) as an oil.

$^1$H NMR (400 MHz, CDCl$_3$) δ 7.13 (dd, 1H, J=5.1, 0.98 Hz), 6.91 (dd, 1H, J=5.0, 3.54 Hz), 6.79 (d, 1H, J=3.4 Hz), 3.40 (dd, 1H, J=12.3, 5.0 Hz), 3.34 (dd, 1H, J=12.2, 5.4 Hz), 2.92 (dd, 1H, J=14.8, 6.9 Hz), 2.88 (dd, 1H, J=14.8, 6.2 Hz), 2.47–2.33 (m, 3H). MS (APCI) m/z 224 (M$^-$–1).

EXAMPLE 9

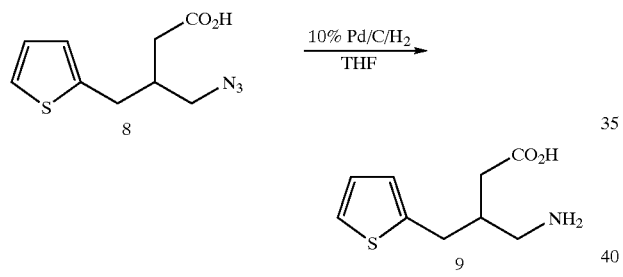

3-Aminomethyl-4-thiophen-2-yl-butyric Acid

A solution of compound 8 (0.70 g, 3.11 mmol) in THF (50 mL) was shaken on a Parr apparatus under a H$_2$ atmosphere (50 psi) for 17 hours. The catalyst was filtered and washed with boiling THF (60 mL) followed by boiling THF/water (40 mL/30 mL). The filtrate was concentrated and the water saturated with NaCl extracted with EtOAc. The water layer rotovapped off and the solids washed with MeOH. The MeOH was evaporated to give a solid which was purified on ion exchange resin (Dowex 50WX8-100 strongly acidic resin) eluting first with water, then with 5% NH$_4$OH. The title compound 9 (0.360 g, 58%) was isolated as a solid.

MP=168–170° C. MS (APCI) m/z 200 (M$^+$+1), 198 (M$^-$–1). Analysis calculated for C$_9$H$_{13}$NO$_2$S: C, 54.25; H, 6.58; N, 7.03; S, 16.09. Found: C, 53.88; H, 6.64; N, 6.86; S, 16.24.

EXAMPLE 10

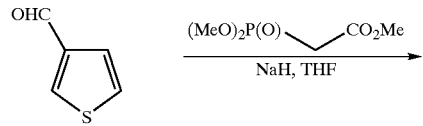

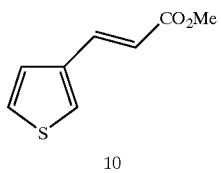

3-Thiophen-3-yl-acrylic Acid Methyl Ester

To a suspension of sodium hydride (3.65 g, 91.22 mmol) in anhydrous THF (250 mL) was added trimethylphosphono acetate (10.16 mL, 62.77 mmol) in THF (50 mL) dropwise. The thick reaction mixture was then stirred for 1 hour. 3 thiophene carboxaldehyde (5.00 mL, 57.01 mmol) was dissolved in THF (50 mL) and added dropwise, and the reaction stirred at room temp for 18 hours. The reaction was quenched with half saturated NH$_4$Cl (120 mL). The layers were separated and the aqueous layer extracted with EtOAc (2×100 mL). The combined organics were washed with brine (100 mL), dried over MgSO$_4$, filtered and concentrated. The crude material was chromatographed on silica eluting with hexanes, then 15% EtOAc/heavens to give the title compound 10 as an oil that crystallizes upon standing (9.05 g, 94%).

$^1$H NMR (400 MHz, CDCl$_3$) δ 7.64 (d, 1H, J=15.7 Hz), 7.46 (d, 1H, J=1.47 Hz), 7.30 (dd, 1H, J=5.13, 2.69 Hz), 7.26 (d, 1H, J=5.13 Hz), 6.22 (d, 1H, J=16.1 Hz), 3.76 (s, 3H). MS (APCI) m/z 169 (M$^+$+1). Analysis calculated for C$_8$H$_8$O$_2$S: C, 57.12; H, 4.79; S, 19.06. Found: C, 57.20; H, 4.77; S, 19.10.

EXAMPLE 11

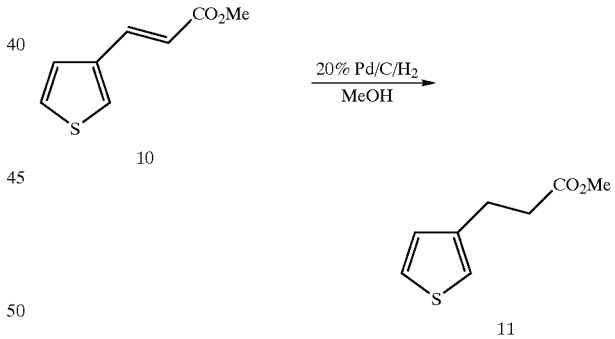

3-Thiophen-3-yl-propionic Acid Methyl Ester

Compound 10 (5.00 g, 29.72 mmol) was combined with 20% Pd/C (0.20 g) and MeOH (150 mL) and stirred under a H$_2$ balloon for 5 hours. Fresh catalyst (0.15 g) was added, and the reaction stirred for 4 hours under an H$_2$ balloon. The catalyst was filtered, washed with EtOAc, and the filtrated concentrated. The crude material was chromatographed on silica eluting with 10% EtOAc/hexanes to give the title compound 11 (4.50 g, 89%) as an oil.

$^1$H NMR (400 MHz, CDCl$_3$) δ 7.22 (m, 1H), 6.94 (m, 1H), 6.90 (m, 1H), 3.64 (s, 3H), 2.94 (t, 2H, J=7.7 Hz), 2.60 (t, 2H, J=7.7 Hz). MS (APCI) m/z 139 (M$^+$–31, -OMe).

EXAMPLE 12

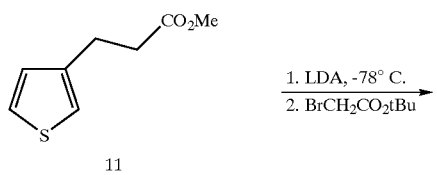

2-Thiophen-3-ylmethyl-succinic Acid 4-tert-butyl Ester 1-methyl Ester

Diisopropyl amine (2.11 mL, 15.0 mmol) was dissolved in anhydrous THF (30 mL) and cooled to −78° C. nBuLi (8.81 mL, 1.6M, 14.1 mmol) was added, and the reaction stirred for 30 minutes at −78° C. Compound 11 (2.00 g, 11.75 mmol) was diluted up in THF (5 mL) and added dropwise to the LDA solution. After addition, the reaction was stirred for 30 minutes at −78° C. t-Butyl bromoacetate (2.60 mL, 17.6 mmol) was dissolved in THF (30 mL) and cooled to −78° C. The LDA solution was added via cannula to the t-butylbromo acetate solution, and the reaction stirred at −78° C. for 90 minutes. The reaction was quenched with saturated $NaH_2PO_4$ and warmed to room temperature. The layers were separated, and the aqueous layer extracted with EtOAc (3×20 mL). The combined organics were dried over $MgSO_4$, filtered and concentrated. The crude oil was chromatographed on $SiO_2$ eluting with 7% EtOAc/hexanes to give the title compound 12 (1.46 g, 44%) as an oil.

$^1$H NMR (400 MHz, $CDCl_3$) δ 7.22 (m, 1H), 6.94 (m, 1H), 6.87 (d, 1H, J=5.1 Hz), 3.63 (s, 3H), 3.03–2.95 (m, 2H), 2.80 (m, 1H), 2.54 (dd, 1H, J=16.4, 8.8 Hz), 2.30 (dd, 1H, J=16.5, 5.0 Hz), 1.38 (s, 9H). MS (APCI) m/z 252 ($M^+$−32, —MeOH), 211 ($M^+$−73, -OtBu).

EXAMPLE 13

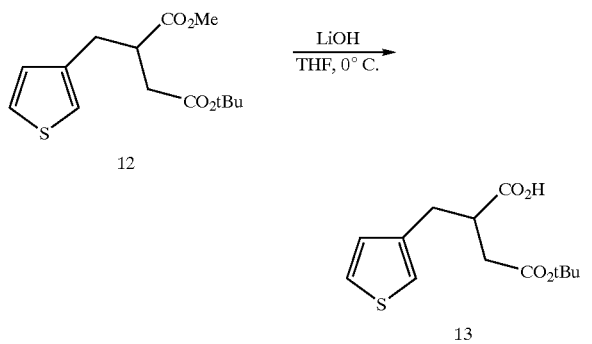

2-Thiophen-3-ylmethyl-succinic Acid 4-tert-butyl Ester

Compound 12 (1.45 g, 5.10 mmol)) was dissolved in THF (20 mL) and cooled in an ice bath. LiOH (7.65 mL, 1N, 7.65 mmol) was added, followed by iPrOH (3 mL). The reaction was stirred at room temperature for 24 hours. Additional LiOH (2.5 mL, 1N) was added, and the reaction stirred for 72 hours. The solvent was removed and the residue diluted with water (25 mL). The water was extracted with ether (2×25 mL), acidified with saturated $NaH_2PO_4$, and extracted with EtOAc (3×50 mL). The combined organics were dried over $MgSO_4$, filtered, and rotovapped to give the title compound 13 (1.142 g, 83%) as an oil.

$^1$H NMR (400 MHz, $CDCl_3$) δ 7.24 (dd, 1H, J=5.2, 2.3 Hz), 6.97 (m, 1H), 6.90 (dd, 1H, J=4.89, 1.22 Hz), 3.14–3.02 (m, 3H), 2.88–2.80 (m, 1H), 2.53 (dd, 1H, J=16.7, 8.7 Hz), 2.33 (dd, 1H, J=16.70, 4.8 Hz), 1.39 (s, 9H).

EXAMPLE 14

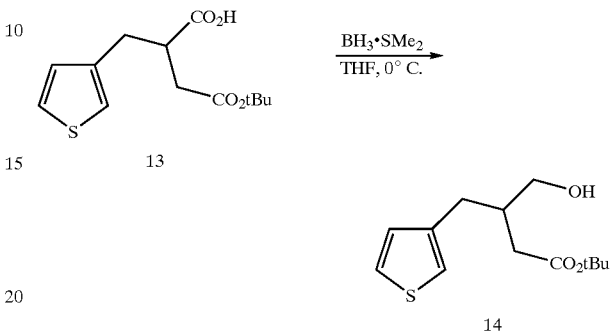

3-Hydroxymethyl-4-thiophen-3-yl-butyric Acid Tert-Butyl Ester

Compound 13 (1.125 g, 4.16 mmol) was dissolved in anhydrous THF (40 mL) and cooled in an ice bath. Borane dimethyl sulfide complex (2.08 mL, 20.8 mmol) was added dropwise, and the reaction stirred at 0° C. for 15 minutes, then at room temperature for 4 hours. The reaction was cooled again in an ice bath and quenched with methanol (25 mL) added dropwise. The solvent was then rotovapped off, and the crude oil chromatographed on silica eluting with 25% EtOAc/hexanes to give the title compound 14 (0.867 g, 81%).

$^1$H NMR (400 MHz, $CDCl_3$) δ 7.22 (m, 1H), 6.94 (m, 1H), 6.91 (dd, 1H, J=4.89, 1.22 Hz), 3.59 (dd, 1H, J=10.99, 4.40 Hz), 3.47 (dd, 1H, J=10.99, 5.86 Hz), 2.69 (dd, 1H, J=14.3, 6.7 Hz), 2.62 (dd, 1H, J=14.1, 6.4 Hz), 2.29–2.24 (m, 3H), 1.85 (br, 1H), 1.42 (s, 9H). MS (APCI) m/z 183 ($M^+$−73, -OtBu).

EXAMPLE 15

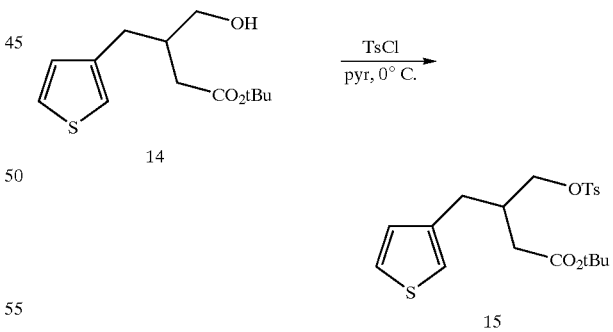

4-Thiophen-3-yl-3-(toluene-4-sulfonyloxymethyl)-butyric Acid Tert-Butyl Ester Compound 14 (0.859 g, 3.35 mmol) was dissolved in anhydrous pyridine (6.5 mL) and cooled to 0° C. Tosyl chloride (0.894 g, 4.69 mmol) was added, and the reaction stirred at 0° C. for 1 hour. The reaction was then placed in a freezer overnight. The reaction was then diluted with EtOAc (100 mL). The solids were filtered and washed with EtOAc (30 mL). The filtrate was then washed with water (40 mL), 1N HCl (30 mL), and then brine (2×30 mL). The organics were dried over MgSO$_4$, filtered, and concentrated to give an oil. This was chromatographed on silica eluting with 15% EtOAc/hexanes to give the title compound 15 (1.227 g, 89%).

$^1$H NMR (400 MHz, CDCl$_3$) δ 7.76 (d, 2H, J=8.42 Hz), 7.34 (d, 2H, J=8.6 Hz) 7.21 (m, 1H), 6.83 (d, 2H, J=4.2 Hz), 3.96 (dd, 1H, J=9.52, 4.76 Hz), 3.89 (dd, 1H, J=9.52, 4.58 Hz), 2.69 (d, 2H, J=6.96 Hz), 2.45 (s, 3H), 2.40 (m, 1H), 2.25 (m, 2H), 1.37 (s, 9H). MS (APCI) m/z 337 (M$^+$–73, –OtBu).

EXAMPLE 16

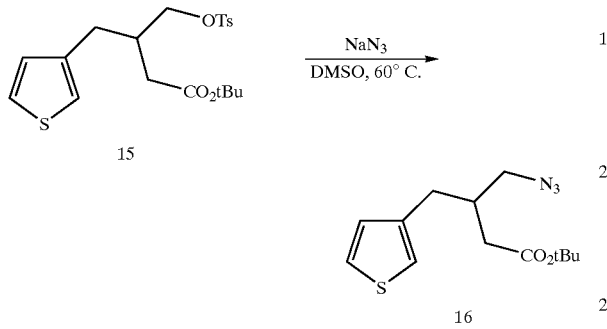

3-Azidomethyl-4-thiophen-3-yl-butyric Acid Tert-Butyl Ester

Compound 15 (1.206 g, 2.94 mmol), NaN$_3$ (0.43 g, 6.76 mmol), and DMSO (14 mL) were combined and heated to 60° C. for 17 hours. Water (75 mL) was added to the reaction and extracted with hexanes (4×75 mL). The combined organics were dried over MgSO$_4$, filtered, and rotovapped to give an oil. The oil was chromatographed on silica eluting with 10% EtOAc/hexanes to give the title compound 16 (0.730 g, 88%) as an oil.

$^1$H NMR (400 MHz, CDCl$_3$) δ 7.23 (dd, 1H, J=4.83, 2.93 Hz), 6.94 (d, 1H, J=2.93 Hz), 6.89 (dd, 1H, J=4.83, 1.22 Hz), 3.28 (dd, 1H, J=12.1, 5.3 Hz), 3.22 (dd, 1H, J=12.1, 5.5 Hz), 2.65 (m, 2H), 2.34–2.83 (m, 1H), 2.22 (m, 2H), 1.42 (s, 9H). MS (APCI) m/z 254 (M$^+$–28, —N$_2$).

EXAMPLE 17

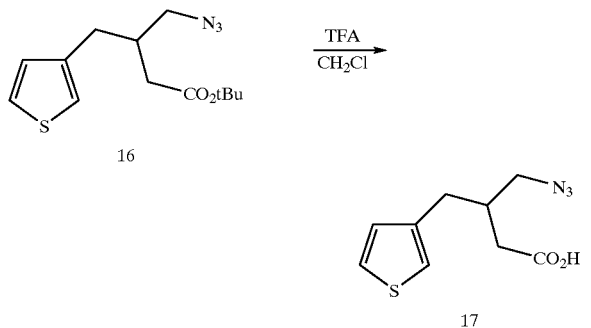

3-Azidomethyl-4-thiophen-3-yl-butyric Acid

Compound 16 (0.730 g, 2.59 mmol) was dissolved in CH$_2$Cl$_2$ (10 mL) and cooled in an ice bath. TFA (2.00 mL, 25.9 mmol) was added dropwise, and the reaction stirred at room temperature for 18 hours. The solvent was rotovapped, water (50 mL) and NaCl added, and the aqueous layer extracted with hexanes (4×50 mL). The extracts were combined, dried over MgSO$_4$, filtered and rotovapped to give the title compound 17 (0.432 g, 79%) as an oil.

$^1$H NMR (400 MHz, CDCl$_3$) δ 7.21 (dd, 1H, J=4.88, 2.93 Hz), 6.92 (d, 1H, J=2.93 Hz), 6.85 (dd, 1H, J=4.88, 1.22 Hz), 3.37 (dd, 1H, J=12.2, 4.88 Hz), 3.23 (dd, 1H, J=12.2, 5.37 Hz), 2.71–2.61 (m, 2H), 2.40–2.27 (m, 3H).

EXAMPLE 18

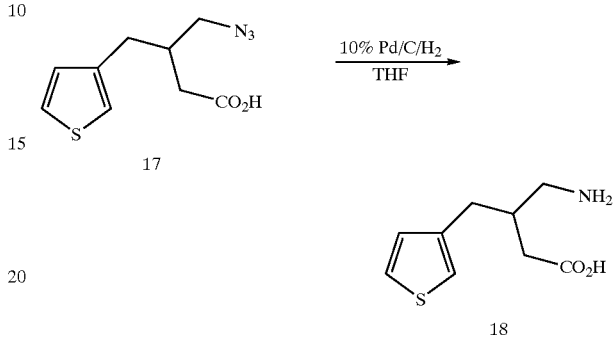

3-Aminomethyl-4-thiophen-3-yl-butyric Acid

Compound 17 (0.42 g, 1.86 mmol), 10% Pd/C (0.50 g) and THF (30 mL) were combined and purged with H$_2$. The reaction was stirred under a H$_2$ balloon for 5 hours. The catalyst was filtered, and washed with boiling MeOH (150 mL). The filtrate was rotovapped to give an off-white solid. The solid was dissolved in EtOH, and passed through celite. The filtrate was rotovapped to give the title compound 18 (0.271 g, 73%) as a tan solid. MP=158–159° C.

Analysis calculated for C$_9$H$_{13}$NO$_2$S 0.52H$_2$O: C, 51.81; H, 6.78; N, 6.71; S, 15.37. Found: C, 51.45; H, 6.77; N, 6.47; S, 14.99.

EXAMPLE 20

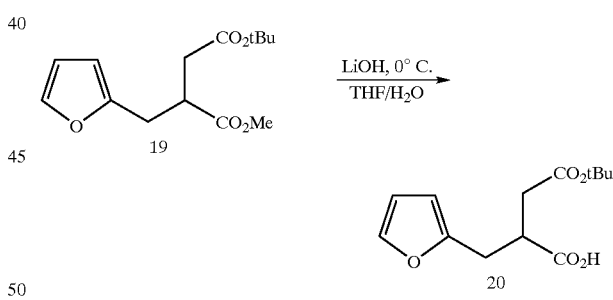

2-Furan-2-ylmethyl-succinic Acid 4-methyl Ester

Compound 19 (1.216 g, 4.53 mmol) was dissolved in THF (18 mL) and cooled in an ice bath. LiOH (9.06 mL, 1N, 9.06 mmol) was added, followed by iPrOH (3 mL). The reaction was stirred at room temperature for 18 hours. The solvent was rotovapped off, and the residue diluted with water (25 mL). The water was extracted with ether (2×25 mL), acidified with 1N HCl, and extracted with EtOAc (3×50 mL). The combined organics were dried over MgSO$_4$, filtered, and rotovapped to give the title compound 20 (1.076 g, 94%) as an oil that crystallized upon standing.

$^1$H NMR (400 MHz, CDCl$_3$) δ 7.28 (m, 1H), 6.24 (d, 1H, J=1.95 Hz), 6.04 (d, 1H, J=3.17 Hz), 3.15–3.02 (m, 2H), 2.86 (dd, 1H, J=14.89, 8.06 Hz), 2.54 (dd, 1H, J=16.85, 8.80 Hz), 2.39 (dd, 1H, J=16.85, 4.88 Hz), 1.39 (s, 9H).

EXAMPLE 21

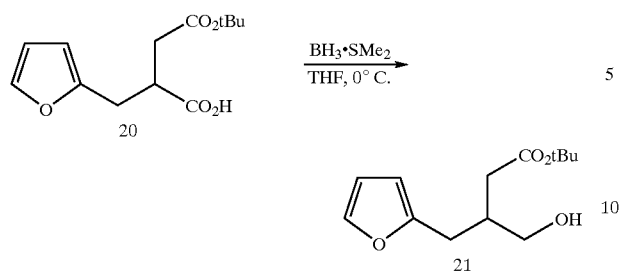

4-Furan-2-yl-3-hydroxymethyl-butyric Acid Methyl Ester

Compound 20 (0.836 g, 3.29 mmol) was dissolved in anhydrous THF (30 mL) and cooled in an ice bath. Borane dimethyl sulfide complex (1.64 mL, 16.4 mmol) was added dropwise, and the reaction stirred at 0° C. for 15 minutes, then at room temperature for 2 hours. The reaction was cooled again in an ice bath and quenched with methanol (20 mL) added dropwise. The solvent was then rotovapped off, and the crude oil chromatographed on silica eluting with 25% EtOAc/hexanes to give the title compound 21 (0.424 g, 55%).

$^1$H NMR (400 MHz, CDCl$_3$) δ 7.29 (dd, 1H, J=1.71, 0.73 Hz), 6.25 (dd, 1H, J=3.17, 1.95 Hz), 6.01 (dd, 1H, J=3.17, 0.73 Hz), 3.62–3.56 (m, 1H), 3.53–3.47 (m, 1H), 2.70 (dd, 1H, J=15.14, 6.84 Hz), 2.64 (dd, 1H, J=15.02, 6.47 Hz), 2.36–2.31 (m, 1H), 2.27–2.25 (m, 2H), 1.95 (t, 1H, J=6.10 Hz), 1.41 (s, 9H

EXAMPLE 22

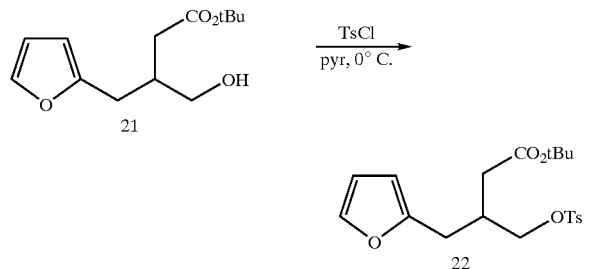

4-Furan-2-yl-3-(toluene-4-sulfonyloxymethyl)-butyric Acid Tert-Butyl Ester

Compound 21 (0.371 g, 1.54 mmol) was dissolved in anhydrous pyridine (5 mL) and cooled to 0° C. Tosyl chloride (0.587 g, 3.08 mmol) was added, and the reaction stirred at 0° C. for 18 hours. The reaction was then diluted with EtOAc (75 mL). The solids were filtered and washed with EtOAc (30 mL). The filtrate was then washed with 1N HCl (50 mL), water (2×50 mL), and then brine (50 mL). The organics were dried over MgSO$_4$, filtered, and rotovapped to give an oil. This was chromatographed on silica eluting with 10% EtOAc/hexanes to give the title compound 22 (0.41 g, 67%).

$^1$H NMR (400 MHz, CDCl$_3$) δ 7.73 (d, 2H, J=8.06 Hz), 7.29 (d, 2H, J=8.06 Hz), 7.20 (m, 1H), 6.19 (m, 1H), 5.91 (m, 1H), 3.99–3.96 (m, 1H), 3.92–3.88 (m, 1H) 2.66–2.64 (m, 2H), 2.45 (m, 1H), 2.41 (s, 3H), 2.27–2.17 (m, 2H), 1.36 (s, 9H).

EXAMPLE 23

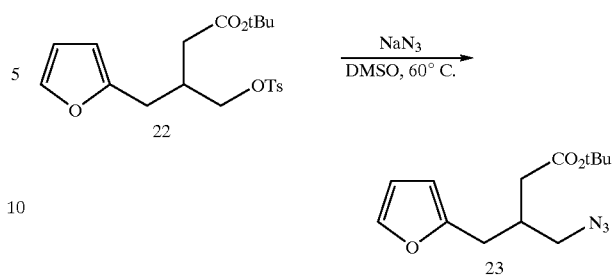

3-Azidomethyl-4-furan-2-yl-butyric Acid Tert-Butyl Ester

Compound 22 (0.85 g, 2.13 mmol), NaN$_3$ (0.375 g, 5.77 mmol), and DMSO (12 mL) were combined and heated to 60° C. for 16 hours. Water (50 mL) and hexanes were added to the reaction and the layers separated. The aqueous layer was extracted with hexanes (4×50 mL). The combined organics were dried over MgSO$_4$, filtered, and concentrated. The crude material was chromatographed on silica eluting with 10% EtOAc/hexanes to give the title compound 23 (0.4.82 g, 85%) as an oil.

$^1$H NMR (400 MHz, CDCl$_3$) δ 7.29 (br, 1H), 6.25 (d, 1H, J=1.71), 6.02 (d, 1H, J=2.44 Hz), 3.31–3.27 (m, 2H), 2.69 (d, 2H, J=6.59 Hz), 2.39 (quintet, 1H, J=6.35 Hz), 2.23 (m, 2H), 1.42 (s, 9H).

EXAMPLE 24

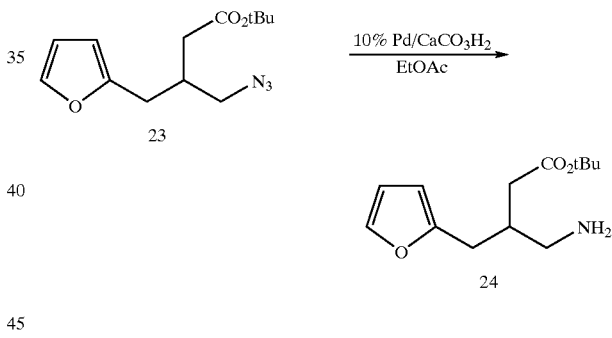

3-Aminomethyl-4-furan-2-yl-butyric Acid Tert-Butyl Ester

Compound 23 (0.482 g, 1.82 mmol) in EtOAc (50 mL) was shaken on a Parr apparatus under a H$_2$ atmosphere (50 psi) for 4 hours. The catalyst was filtered and washed with EtOAc. The filtrate was concentrated and the crude material chromatographed on silica eluting with MeOH to give the title compound 24 (0.335 g, 77%) as an oil.

$^1$H NMR (400 MHz, CDCl$_3$) δ 7.27 (dd, 1H, J=1.71, 0.73 Hz), 6.24 (dd, 1H, J=3.17, 1.95 Hz), 6.00 (dd, 1H, J=3.17, 0.73 Hz), 2.71–2.56 (m, 4H), 2.25–2.14 (m, 3H), 1.41 (s, 9H), 1.37 (br, 2H).

EXAMPLE 25

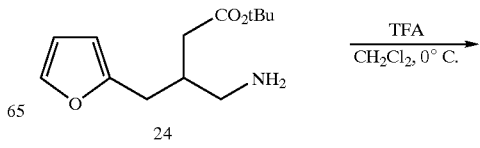

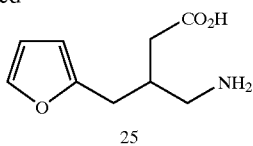

3-Aminomethyl-4-furan-2-yl-butyric Acid

Compound 24 (0.318 g, 1.329 mmol) was dissolved in CH$_2$Cl$_2$ (6 mL) and cooled in an ice bath. TFA (0.51 mL, 6.645 mmol) was added dropwise, and the reaction stirred at room temperature for 24 hours. The solvent was rotovapped, water (50 mL) and NaCl added, and the aqueous layer extracted with hexanes (4×50 mL). The extracts were combined, dried over MgSO$_4$, filtered and rotovapped. The crude material was passed through an ion exchange resin (Dowex 50WX8-100 strongly acidic resin) eluting first with water, then with 5% NH$_4$OH to give the title compound the title compound 25 as an oil. The material was used as is in the next step.

EXAMPLE 26

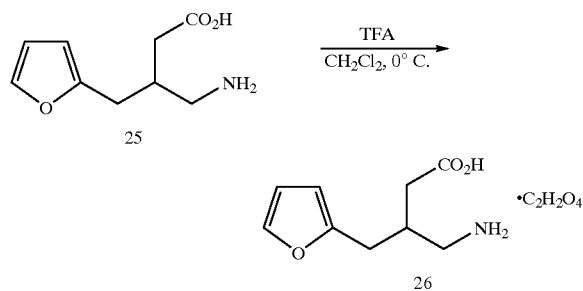

3-Aminomethyl-4-furan-2-yl-butyric Acid Oxalic Acid Salt

Compound 25 (0.299 g, 1.632 mmol) was dissolved in EtOH (5 mL). Oxalic acid (0.206 g, 1.632 mmol) was dissolved in EtOH (1 mL) and added to 25. The mixture was stirred at room temperature for 1 hour. The solvent was rotovapped, and the residue dissolved in minimal water and added dropwise to acetone (150 mL). The solids were filtered off, and the filtrate concentrated to give a solid. The solids were filtered and washed with some acetone to give the title compound 26 (0.248 g, 56%) as the oxalate salt.

MP=128–133° C. Analysis calculated for C$_9$H$_{13}$NO$_3$·1.3 C$_2$H$_2$O$_4$: C, 46.40; H, 5.24; N, 4.67. Found: C, 46.30; H, 5.19; N, 4.35.

EXAMPLE 27

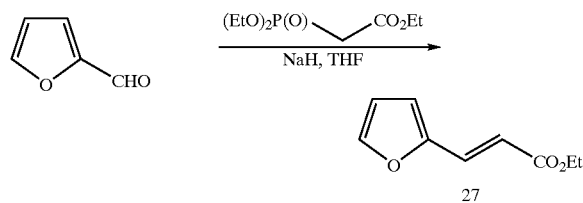

3-Furan-2-yl-acrylic Acid Ethyl Ester

To a suspension of sodium hydride (9.96 g, 249.1 mmol) in anhydrous THF (500 mL) at 0° C. was added triethylphosphono acetate (45.3 mL, 228.4 mmol) in THF (80 mL) dropwise. The reaction mixture was then stirred for 30 minutes. 2-Furaldehyde (17.2 mL, 207.6 mmol) was dissolved in THF (33 mL) and added dropwise to the reaction at 0° C. The reaction was stirred at room temp for 3 hours, and then quenched with saturated NH$_4$Cl (160 mL). The layers were separated and the aqueous layer extracted with EtOAc (2×100 mL). The combined organics were washed with brine (100 mL), dried over MgSO$_4$, filtered and concentrated. The crude material was chromatographed on silica eluting with 10% EtOAc/hexanes to give the title compound 27 as an oil (30.4 g, 90%).

$^1$H NMR (400 MHz, CDCl$_3$) δ 7.45 (m, 1H), 7.40 (d, 1H, J=15.9 Hz), 6.57 (d, 1H, J=3.42 Hz), 6.43 (m, 1H), 6.28 (d, 1H, J=15.9 Hz), 4.21 (q, 2H, J=7.2 Hz), 1.29 (t, 3H, J=7.2 Hz). MS (APCI) m/z 167 (M$^+$+1).

EXAMPLE 28

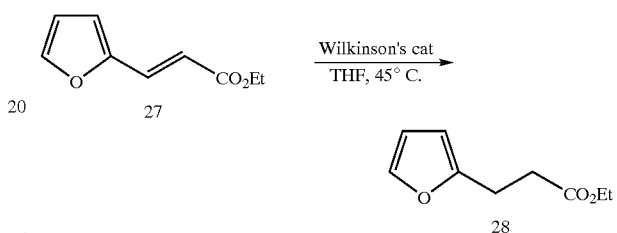

3-Furan-2-yl-propionic Acid Ethyl Ester

A solution of compound 27 (30.60 g, 184.15 mmol) and Wilkinson's catalyst (0.5 g) in THF (250 mL) was shaken on a Parr apparatus under a H$_2$ atmosphere (50 psi) for 18 hours at 45° C. The solvent was concentrated and the crude material chromatographed on silica eluting with 10% EtOAc/hexanes to give the title compound 28 as an oil (30.00 g, 97%).

$^1$H NMR (400 MHz, CDCl$_3$) δ 7.30 (dd, 1H, J=1.83, 0.73 Hz), 6.27 (dd, 1H, J=1.83, 3.1 Hz), 6.01 (dd, 1H, J=3.11, 0.92 Hz), 4.14 (q, 2H, J=7.14 Hz), 2.97 (dd, 2H, J=7.32, 7.87 Hz), 2.64 (dd, 2H, J=8.79, 7.87 Hz), 1.25 (t, 3H, J=7.14 Hz). (APCI) m/z 169 (M$^+$+1).

EXAMPLE 29

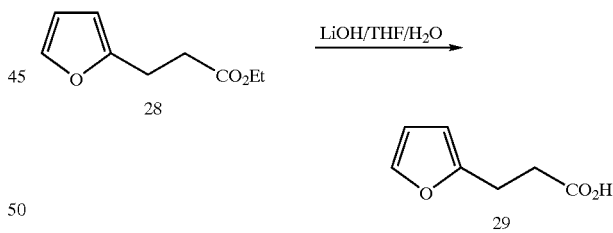

3-Furan-2-yl-propionic Acid

Compound 28 (15.033 g, 89.38 mmol) was dissolved in THF (250 mL) and cooled in an ice bath. LiOH (132.8 mL, 1N, 132.8 mmol) was added, followed by iPrOH (50 mL). The reaction was stirred at room temperature for 18 hours. The solvent was rotovapped off, and the residue diluted with water (100 mL). The water was extracted with ether (2×75 mL), and then acidified with 1N HCl. The aqueous layer was extracted with EtOAc (4×100 mL). The organics were combined, dried over MgSO$_4$, filtered and rotovapped to give the title compound 29 (12.873 g, ~100%) as a white solid.

$^1$H NMR (400 MHz, CDCl$_3$) δ 7.29 (2, 1H, J=1.22 Hz), 6.22 (dd, 1H, J=3.17, 1.95 Hz), 6.02 (dd, 1H, J=3.17, 0.73 Hz), 2.96 (t, 2H, J=7.57 Hz), 2.70 (t, 2H, J=7.57 Hz).

EXAMPLE 30

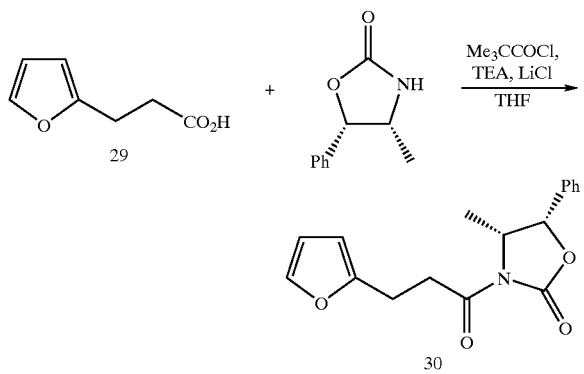

[4R-(4α,5α)]3-(3-Furan-2-yl-propionyl)-4-methyl-5-phenyl-oxazolidin-2-one

Compound 29 (11.04 g, 78.82 mmol) was dissolved in THF (190 mL) and cooled in an ice bath. Triethyl amine (41.2 mL, 295.6 mmol) was added, followed by the trimethylacetyl chloride (14.6 mL, 118.23 mmol). The reaction was stirred at 0° C. for 90 minutes, and the LiCl (3.765 g, 86.70 mmol), (4R,5S)-(+)-4-methyl-5-phenyl-2-oxazolidinone (14.24 g, 80.4 mmol), and THF (70 mL) were added. The reaction was stirred at room temperature overnight. The solids were filtered, washed with EtOAc, and the filtrate and washings rotovapped to give a brown colored suspension. The solids were filtered, washed with EtOAc, and the filtrated rotovapped. The crude material was chromatographed on silica eluting with 10% EtOAc/hexanes to give the title compound 30 (15.57 g, 66%) as an off-white solid.

$^1$H NMR (400 MHz, CDCl$_3$) δ 7.42–7.33 (m, 3H), 7.29–7.24 (m, 3H), 6.26 (m, 1H), 6.04 (d, 1H, J=3.17), 5.65 (d, 1H, J=7.33 Hz), 4.74 (q, 1H, J=6.8 Hz), 3.35–3.21 (m, 2H), 3.01 (t, 2H, J=7.4 Hz), 0.87 (d, 3H, J=6.59 Hz).

MS (APCI) m/z 300 (M$^+$+1). Analysis calculated for C$_{17}$H$_{17}$NO$_4$: C, 68.22; H, 5.72; N, 4.68. Found: C, 68.32; H, 5.71; N, 4.59. [α]$_D$=+36.6° (c=1 in CHCl$_3$).

EXAMPLE 31

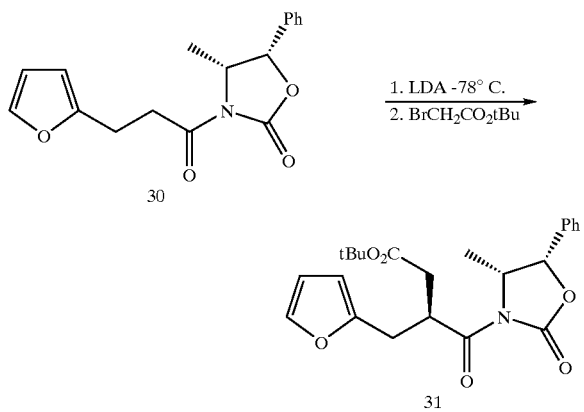

(S)-3-Furan-2-ylmethyl-4-([4S-(4α,5α)]4-methyl-2-oxo-5-phenyl-oxazolidin-3-yl)-4-oxo-butyric Acid Tert-Butyl Ester Diisopropyl amine (1.37 mL, 9.77 mmol) was dissolved in anhydrous THF (20 mL) and cooled to 0° C. nBuLi (5.64 mL, 1.6 M, 9.02 mmol) was added, and the mixture stirred for 30 minutes at 0° C., and then cooled to −78° C. Compound 30 (2.50 g, 8.35 mmol) was diluted up in TBF (5 mL) and added dropwise to the LDA solution. After addition, the reaction was stirred for 30 minutes at −78° C. t-Butyl bromoacetate was passed through a neutral Al$_2$O$_3$ plug, was dissolved (1.67 mL, 11.28 mmol) in THF (20 mL) and cooled to −78° C. The LDA solution was added via cannula to the t-butylbromo acetate solution, and the reaction stirred at −78° C. for 30 minutes, then allowed to warm to room temperature. The reaction was quenched with saturated NaH$_2$PO$_4$. The layers were separated, and the aqueous layer extracted with EtOAc (3×25 mL). The combined organics were dried over MgSO$_4$, filtered and rotovapped. The crude material was chromatographed on SiO$_2$ eluting with 10% EtOAc/hexanes to give the title compound 31 (2.60 g, 75%) as an oil.

$^1$H NMR (400 MHz, CDCl$_3$) δ 7.41–7.24 (m, 6H), 6.27 (d, 1H, J=1.95 Hz), 6.09 (d, 1H, J=3.17 Hz), 5.52 (d, 1H, J=7.08 Hz), 4.67 (quin, 1H, J=6.7 Hz), 4.54 4.50 (m, 1H), 2.97 (dd, 1H, J=14.8, 7.0 Hz), 2.88–2.77 (m, 2H), 2.42 (dd, 1H, J=16.7, 4.5 Hz), 1.37 (s, 9H), 0.87 (d, 3H, J=6.37 Hz). [α]$_D$–5.5° (c=1 in CHCl$_3$).

EXAMPLE 32

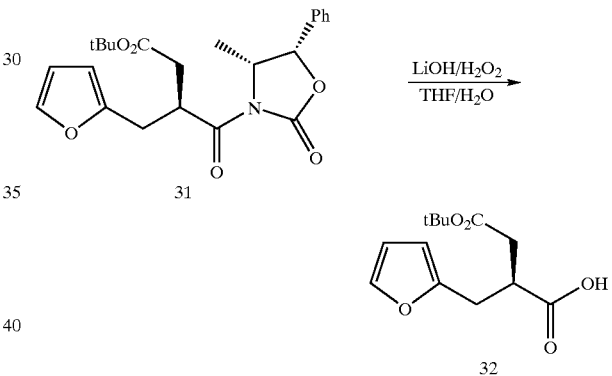

(S)-2-Furan-2-ylmethyl-succinic Acid 4-tert-butyl Ester

Compound 31 (5.457 g, 13.20 mmol) was dissolved in THF (63 mL)/H$_2$O (16 mL) and cooled in an ice bath. The H$_2$O$_2$ (2.33 mL, 35%, 26.40 mmol) and LiOH (1N, 26.40 mL) were premixed, and then added dropwise to the THF/H$_2$O. The reaction was stirred at 0° C. for 4 hours and then quenched with NaHSO$_3$ (15 g). The reaction was stirred at room temperature overnight. The THF was rotovapped off, water added (100 mL) to the residue, and the water acidified to PH=3 with 3N HCl. The aqueous layer was extracted with EtOAc (4×75 mL), and the combined organics dried over MgSO$_4$, filtered, and rotovapped to give an oil. The oil was dissolved in EtOAc (10 mL), and heptane (250 mL) added to precipitate the oxazolidinone. The solution was stirred for 1 hour, and the solids filtered off. The organic filtrate was washed with water (100 mL, 60° C.). The organic layer was dried over MgSO$_4$, filtered, and rotovapped to give the title compound 32 (2.603 g, 78%) as an oil.

$^1$H NMR (400 MHz, CDCl$_3$) δ 7.29 (d, 1H, J=0.98 Hz), 6.26 (m, 1H), 6.05 (d, 1H, J=2.93 Hz) 3.14–3.04 (m, 2H), 2.87 (dd, 1H, J=15.0, 7.94 Hz), 2.57 (dd, 1H, J=16.8, 8.55 Hz), 2.40 (dd, 1H, J=16.8, 4.88 Hz), 1.41 (s, 9H).

EXAMPLE 33

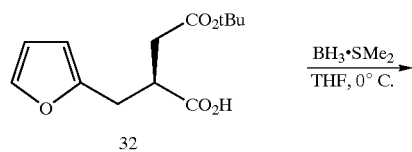

(S)-4-Furan-2-yl-3-hydroxymethyl-butyric Acid Tert-Butyl Ester

Compound 32 (2.603 g, 10.24 mmol) was dissolved in anhydrous THF (100 mL) and cooled in an ice bath. Borane dimethyl sulfide complex (3.1 mL, 31 mmol) was added dropwise, and the reaction stirred at 0° C. for 15 minutes, then at room temperature for 2 hours. The reaction was cooled again in an ice bath and quenched with methanol (20 mL) added dropwise, and then stirred at room temperature for 1 hour. The solvent was then rotovapped off, and the crude oil chromatographed on silica eluting with EtOAc/hexanes gradient (10% EtOAc for 10 minutes, gradient to 25% EtOAc at 25 minutes) to give the title compound 33 (1.852 g 75%) as an oil.

$^1$H NMR (400 MHz, CDCl$_3$) δ 7.29 (d, 1H, J=0.49 Hz), 6.26 (d, 1H, J=1.95 Hz), 6.03 (d, 1H, J=3.17 Hz), 3.60 (quin, 1H, J=5.37 Hz), 3.52 (quin, 1H, J=5.74 Hz), 2.72 (dd, 1H, J=15.1, 6.84 Hz), 2.66 (dd, 1H, J=15.3, 6.71 Hz), 2.38–2.32 (m, 1H), 2.28–2.26 (m, 2H), 1.97 (t, 1H, J=5.98 Hz), 1.43 (s, 9H) MS (APCI) m/z 241 (M$^+$+1). [α]$_D$+2.3° (c=1 in CHCl$_3$).

EXAMPLE 34

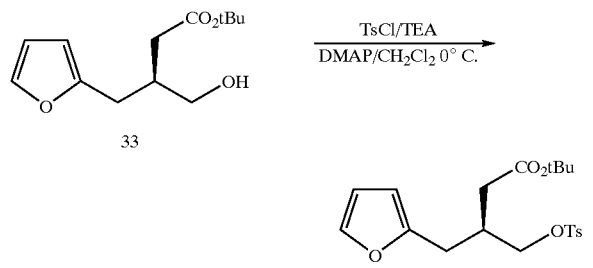

(S)-4-Furan-2-yl-3-(toluene-4-sulfonyloxymethyl)-butyric Acid Tert-Butyl Ester Compound 33 (1.822 g, 7.58 mmol) was dissolved in anhydrous CH$_2$Cl$_2$ (27 mL) and cooled to 0° C. DMAP (catalytic) was added followed by tosyl chloride (1.73 g, 9.10 mmol). Triethylamine (2.32 mL, 16.68 mmol) was added dropwise, and the reaction stirred at 0° C. for 18 hours. The reaction was then diluted with EtOAc (75 mL). The solvent was rotovapped, and the residue suspended in EtOAc. The solids were filtered and washed with EtOAc (30 mL). The organics were dried over MgSO$_4$, filtered, and rotovapped to give an oil. This was chromatographed on silica eluting with 5% EtOAc/hexanes gradient to 20% EtOAc/hexanes to give the title compound 34 (2.85 g, 95%) as an oil.

$^1$H NMR (400 MHz, CDCl$_3$) δ 7.75 (d, 2H, J=8.06 Hz), 7.32 (d, 2H, J=8.06 Hz), 7.22 (s, 1H), 6.20 (d, 1H, J=1.71 Hz), 5.92 (d, 1H, J=2.93 Hz)), 3.99 (dd, 1H, J=9.64, 5.01 Hz), 3.91 (dd, 1H, J=9.64, 5.01 Hz), 2.71–2.61 (m, 2H), 2.47 (m, 1H), 2.43 (s, 3H), 2.25 (dd, 1H, J=16.5, 7.2 Hz), 2.19 (dd, 1H, J=16.4, 6.8 Hz), 1.38 (s, 9H).

EXAMPLE 35

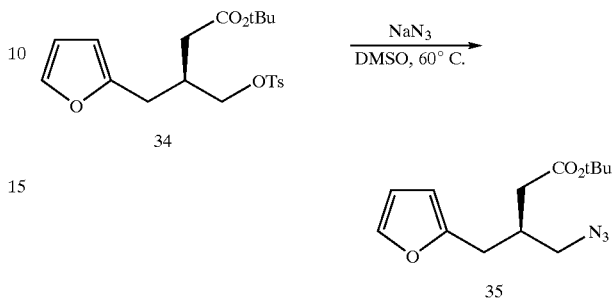

(S)-3-Azidomethyl-4-furan-2-yl-butyric Acid Methyl Ester

Compound 34 (2.840 g, 7.20 mmol), NaN$_3$ (1.287 g, 19.80 mmol), and DMSO (13 mL) were combined and heated to 60° C. for 6 hours. EtOAc (100 mL) was added and the solids filtered. The filtrate was rotovapped, and the crude material was chromatographed on silica eluting with 10% EtOAc/hexanes to give the title compound 35 (1.75 g, 92%) as an oil.

$^1$H NMR (400 MHz, CDCl$_3$) δ 7.30 (br s, 1H), 6.27 (br s, 1H), 6.04 (d, 1H, J=2.69 Hz), 3.34 (dd, 1H, J=12.2, 5.62 Hz), 3.27 (dd, 1H, J=12.1, 5.74 Hz), 2.69 (d, 2H, J=6.59 Hz), 2.40 (quintet, 1H, J=6.47 Hz), 2.25 (d, 2H, J=7.1 Hz), 1.43 (s, 9H). MS (APCI) m/z 238 (M$^+$-28, —N$_2$).

EXAMPLE 36

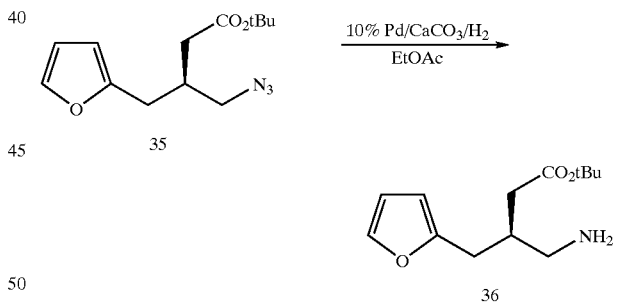

(S)-3-Aminomethyl-4-furan-2-yl-butyric Acid Tert-Butyl Ester

Compound 35 (1.74 g, 6.56 mmol) in EtOAc (50 mL) was shaken on a Parr apparatus under a H$_2$ atmosphere (50 psi) for 2 hours. The catalyst was filtered and washed with EtOAc. The filtrate was rotovapped, and the crude material chromatographed on silica eluting with EtOAc (10 minutes), then gradient to MeOH (100% at 25 minutes) to give the title compound 36 (1.325 g, 84%) as an oil.

$^1$H NMR (400 MHz, CDCl$_3$) δ 7.28 (br s, 1H), 6.26 (d, 1H, J=1.71 Hz), 6.01 (d, 1H, J=2.69 Hz), 2.68–2.61 (m, 4H), 2.23–2.16 (m, 3H), 1.42 (s, 9H), 1.15 (br, 2H). MS (APCI) m/z 240 (M$^+$+1).

EXAMPLE 37

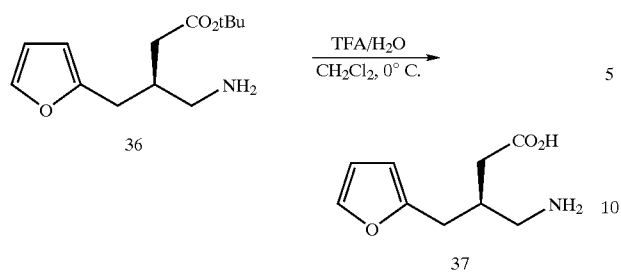

(S)-3-Aminomethyl-4-furan-2-yl-butyric Acid

Compound 36 (1.325 g, 5.54 mmol) was dissolved in CH$_2$Cl$_2$/water (60 mL/2 mL)) and cooled in an ice bath. TFA (10.6 mL, 138 mmol) was added dropwise, and the reaction warmed to room temperature. The reaction was stirred for 2 hours more. The solvent was rotovapped, and the crude material passed through an ion exchange resin (Dowex 50WX8-100 strongly acidic resin) eluting first with water, then with 5% NH$_4$OH to give the title compound 37 (0.53 g, 52%) as a solid.

MP=151–153° C. Analysis calculated for C$_9$H$_{13}$NO$_3$: C, 59.00; H, 7.15; N, 7.65. Found: C, 58.65; H, 7.17; N, 7.37. [α]$_D$+6.40 (c=1 in H$_2$O).

EXAMPLE 38

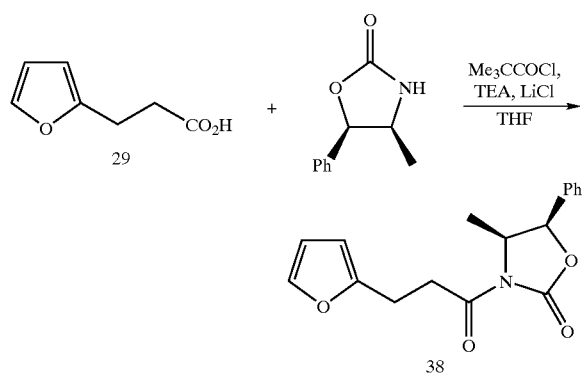

[4S-((4α,5α)]3-(3-Furan-2-yl-propionyl)-4-methyl-5-phenyl-oxazolidin-2-one

Compound 29 (11.66 g, 83.19 mmol) was dissolved in THF (190 mL) and cooled in an ice bath. Triethyl amine (43.5 mL, 312.1 mmol) was added, followed by the trimethylacetyl chloride (15.4 mL, 125.0 mmol). The reaction was stirred at 0° C. for 2 hours, and the LiCl (3.879 g, 91.5 mmol), (4S,5R)-(−)-4-methyl-5-phenyl-2-oxazolidinone (15.02 g, 84.76 mmol), and THF (70 mL) were added. The reaction was stirred at room temperature overnight. The solids were filtered, washed with EtOAc, and the filtrate and washings rotovapped to give a brown colored suspension. The solids were filtered, washed with EtOAc, and the filtrated rotovapped. The crude material was chromatographed on silica eluting with 10% EtOAc/hexanes to give the title compound 38 (19.967 g, 80%) as an off-white solid.

$^1$H NMR (400 MHz, CDCl$_3$) δ 7.42–7.33 (m, 3H), 7.29–7.24 (m, 3H), 6.26 (m, 1H), 6.04 (d, 1H, J=3.17), 5.65 (d, 1H, J=7.33 Hz), 4.74 (q, 1H, J=6.8 Hz), 3.35–3.21 (m, 2H), 3.01 (t, 2H, J=7.4 Hz), 0.87 (d, 3H, J=6.59 Hz). MS (APCI) m/z 300 (M$^+$+1).

Analysis calculated for C$_{17}$H$_{17}$NO$_4$: C, 68.22; H, 5.72; N, 4.68. Found: C, 68.34; H, 5.81; N, 4.63. [α]$_D$=−39.5° (c=1 in CHCl$_3$).

EXAMPLE 39

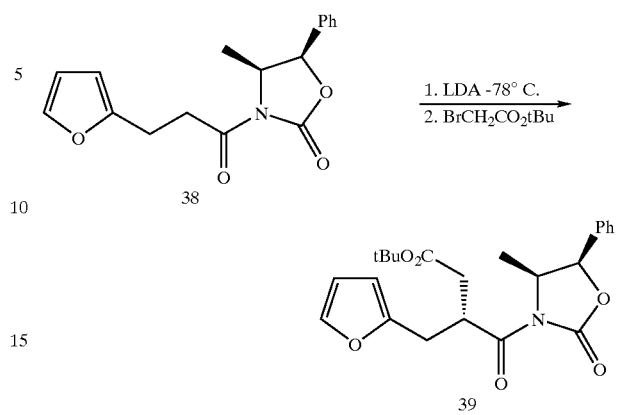

(R)-3-Furan-2-ylmethyl-4-([4S-(4α,5α)]4-methyl-2-oxo-5-phenyl-oxazolidin-3-yl)-4-oxo-butyric Acid Tert-Butyl Ester Diisopropyl amine (3.04 mL, 21.69 mmol) was dissolved in anhydrous THF (40 mL) and cooled to 0° C. nBuLi (12.53 mL, 1.6 M, 20.05 mmol) was added, and the mixture stirred for 30 minutes at 0° C., and then cooled to −78° C. Compound 38 (5.00 g, 16.70 mmol) was diluted up in THF (10 mL) and added dropwise to the LDA solution. After addition, the reaction was stirred for 30 minutes at −78° C. t-Butyl bromoacetate was passed through a neutral Al$_2$O$_3$ plug, was dissolved (3.21 mL, 21.74 mmol) in THF (40 mL) and cooled to −78° C. The LDA solution was added via cannula to the t-butylbromo acetate solution, and the reaction stirred at −78° C. for 30 minutes, then allowed to warm to room temperature. The reaction was quenched with saturated NaH$_2$PO$_4$. The layers were separated, and the aqueous layer extracted with EtOAc (3×75 mL). The combined organics were dried over MgSO$_4$, filtered and rotovapped. The crude material was chromatographed on SiO$_2$ eluting with 5% EtOAc/hexanes (5 minutes), then gradient to 15% EtOAc/hexanes (at 20 minutes) to give the title compound 39 (4.528 g, 67%) as an oil.

$^1$H NMR (400 MHz, CDCl$_3$) δ 7.41–7.24 (m, 6H), 6.27 (br s, 1H), 6.09 (br s, 1H), 5.53 (d, 1H, J=7.32 Hz), 4.67 (quin, 1H, J=6.71 Hz), 4.54–4.50 (m, 1H), 2.98 (dd, 1H, J=15.0, 6.71 Hz), 2.88–2.77 (m, 2H), 2.42 (dd, 1H, J=16.6, 4.64 Hz), 1.38 (s, 9H), 0.87 (d, 3H, J=6.59 Hz). [α]$_D$+8.2° (c=1 in CHCl$_3$).

EXAMPLE 40

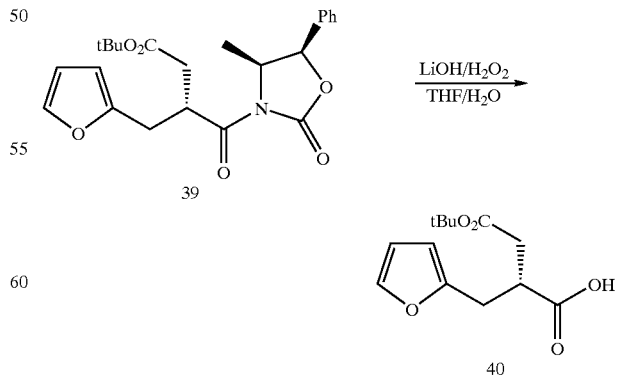

(R)-2-Furan-2-ylmethyl-succinic Acid 4-tert-butyl Ester

Compound 39 (4.452 g, 10.77 mmol) was dissolved in THF (52 mL)/H$_2$O (13 mL) and cooled in an ice bath. The H₂O₂ (1.90 mL, 35%, 21.54 mmol) and LiOH (1N, 21.54 mL) were premixed, and then added dropwise to the THF/H₂O. The reaction was stirred at 0° C. for 4 hours and then quenched with NaHSO₃ (13 g). The reaction was stirred at room temperature overnight. The THF was rotovapped off, water added (100 mL) to the residue, and the water acidified to pH=3 with 3N HCl. The aqueous layer was extracted with EtOAc (4×75 mL), and the combined organics dried over MgSO₄, filtered, and rotovapped to give an oil containing 40 and the chiral auxiliary. The crude material was used as is without further purification in the next step.

EXAMPLE 41

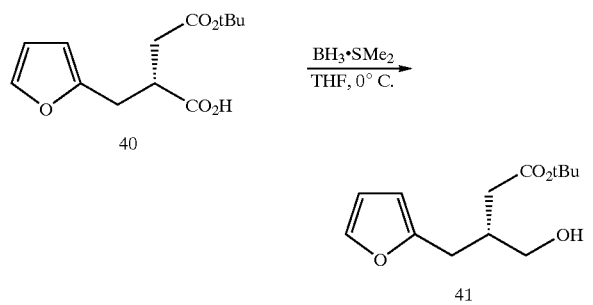

(R)-4-Furan-2-yl-3-hydroxymethyl-butyric Acid Tert-Butyl Ester

The crude material from example 40 was dissolved in anhydrous THF (100 mL) and cooled in an ice bath. Borane dimethyl sulfide complex (3.2 mL, 32 mmol) was added dropwise, and the reaction stirred at 0° C. for 15 minutes, then at room temperature for 2 hours. The reaction was cooled again in an ice bath and quenched with methanol (15 mL) added dropwise, and then stirred at room temperature for 1 hour. The solvent was then rotovapped off, and the crude oil chromatographed on silica eluting with EtOAc/hexanes gradient (7% EtOAc for 5 minutes, gradient to 15% EtOAc at 20 minutes) to give the title compound 41 (1.865 g 75% from example 39) as an oil.

¹H NMR (400 MHz, CDCl₃) δ 7.29 (dd, 1H, J=1.83, 0.85 Hz), 6.26 (dd, 1H, J=3.05, 1.83 Hz), 6.02 (dd, 1H, J=3.05, 0.61 Hz), 3.60 (quin, 1H, J=5.37 Hz), 3.52 (quin, 1H, J=5.68 Hz), 2.72 (dd, 1H, J=15.0, 6.71 Hz), 2.66 (dd, 1H, J=15.1, 6.35 Hz), 2.38–2.32 (m, 1H), 2.28–2.26 (m, 2H), 1.94 (t, 1H, J=5.98 Hz), 1.43 (s, 9H).

MS (APCI) m/z 241 (M⁺+1). [α]$_D$ −2.1° (c=1 in CHCl₃).

EXAMPLE 42

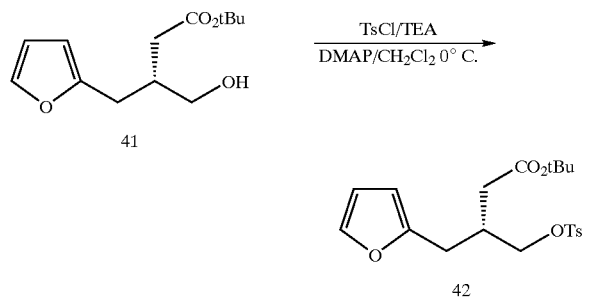

(R)-4-Furan-2-yl-3-(toluene-4-sulfonyloxymethyl)-butyric Acid Tert-Butyl Ester

Compound 41 (1.831 g, 7.62 mmol) was dissolved in anhydrous CH₂Cl₂ (27 mL) and cooled to 0° C. DMAP (catalytic) was added followed by tosyl chloride (1.74 g, 9.14 mmol). Triethylamine (2.32 mL, 16.76 mmol) was added dropwise, and the reaction stirred at 0° C. for 28 hours. The reaction was then diluted with EtOAc (75 mL). The solvent was rotovapped, and the residue suspended in EtOAc. The solids were filtered and washed with EtOAc (30 mL). The organics were washed with 1N HCl (25 mL), saturated NaHCO₃ (30 mL), brine (30 mL), dried over MgSO₄, filtered, and rotovapped to give an oil. This was chromatographed on silica eluting with EtOAc/hexanes gradient (5% for 5 minutes to 10% at 10 minutes to 20% at 25 minutes) to give the title compound 42 (2.81 g, 94%) as an oil.

¹H NMR (400 MHz, CDCl₃) δ 7.75 (d, 2H, J=8.06 Hz), 7.31 (d, 2H, J=7.81 Hz), 7.22 (br s, 1H), 6.20 (br s, 1H), 5.92 (d, 1H, J=2.44 Hz), 3.99 (dd, 1H, J=9.64, 5.01 Hz), 3.91 (dd, 1H, J=9.52, 4.88 Hz), 2.71–2.61 (m, 2H), 2.47 (m, 1H), 2.42 (s, 3H), 2.25 (dd, 1H, J=16.5, 7.2 Hz), 2.19 (dd, 1H, J=16.4, 6.8 Hz), 1.38 (s, 9H).

EXAMPLE 43

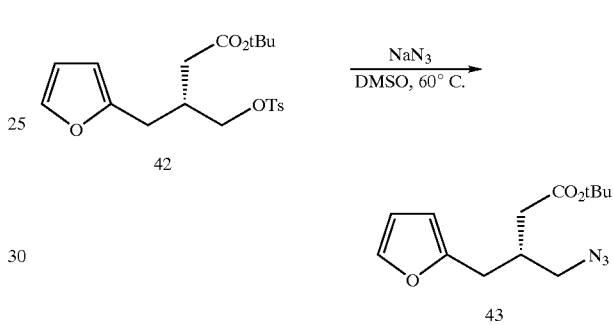

(R)-3-Azidomethyl-4-furan-2-yl-butyric Acid Tert-Butyl Ester

Compound 42 (2.70 g, 6.845 mmol), NaN₃ (1.224 g, 18.82 mmol), and DMSO (12 mL) were combined and heated to 60° C. for 6 hours. EtOAc (100 mL) was added and the solids filtered. The filtrate was rotovapped, and the crude material was chromatographed on silica eluting with 10% EtOAc/hexanes to give the title compound 43 (1.505 g, 83%) as an oil.

¹H NMR (400 MHz, CDCl₃) δ 7.30 (br s, 1H), 6.27 (br s, 1H), 6.04 (d, 1H, J=2.69 Hz), 3.33 (dd, 1H, J=12.3, 5.49 Hz), 3.27 (dd, 1H, J=12.2, 5.86 Hz), 2.69 (d, 2H, J=6.59 Hz), 2.40 (quintet, 1H, J=6.35 Hz), 2.25 (d, 2H, J=6.8 Hz), 1.43 (s, 9H). MS (APCI) m/z 238 (M⁺-28, —N₂).

EXAMPLE 44

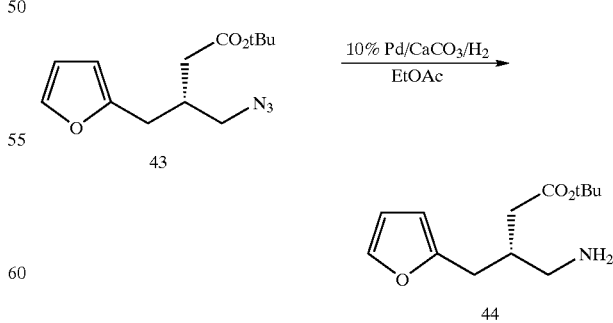

(R)-3-Aminomethyl-4-furan-2-yl-butyric Acid Tert-Butyl Ester

Compound 43 (1.50 g, 5.65 mmol) in EtOAc (50 mL) was shaken on a Parr apparatus under a H₂ atmosphere (50 psi)

for 2.5 hours. The catalyst was filtered and washed with EtOAc. The filtrate was rotovapped, and the crude material chromatographed on silica eluting with EtOAc (10 minutes), then gradient to MeOH (100% at 25 minutes) to give the title compound 44 (1.133 g, 84%) as an oil.

$^1$H NMR (400 MHz, CDCl$_3$) δ 7.28 (d, 1H, J=0.98 Hz), 6.25 (d, 1H, J=1.95 Hz), 6.01 (d, 1H, J=2.93 Hz), 2.69–2.61 (m, 4H), 2.23–2.18 (m, 3H), 1.42 (s, 9H), 1.15 (br, 2H). MS (APCI) m/z 240 (M$^+$+1).

EXAMPLE 45

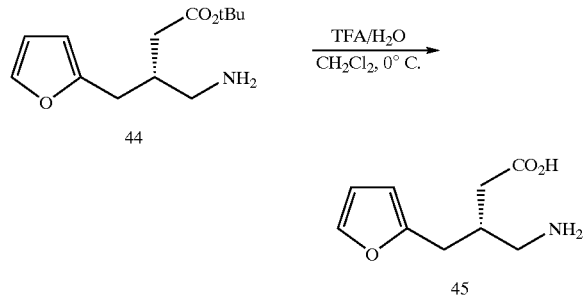

(R)-3-Aminomethyl-4-furan-2-yl-butyric Acid

Compound 44 (1.117 g, 4.67 mmol) was dissolved in CH$_2$Cl$_2$/water (52 mL/1.73 mL) and cooled in an ice bath. TFA (9.0 mL, 1116.8 mmol) was added dropwise, and the reaction warmed to room temperature. The reaction was stirred for 2 hours more. The solvent was rotovapped, and the crude material passed through an ion exchange resin (Dowex 50WX8-100 strongly acidic resin) eluting first with water, then with 5% NH$_4$OH to give the title compound 45 (0.603 g, 71%) as a solid.

MP=151–153° C. Analysis calculated for C$_9$H$_{13}$NO$_3$: C, 59.00; H, 7.15; N, 7.65. Found: C, 58.85; H, 7.13; N, 7.47. [α]$_D$ –6.0° (c=1 in H$_2$O).

What is claimed is:

1. A compound of formula:

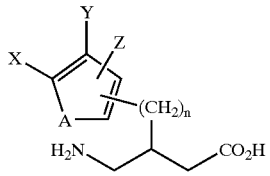

or a pharmaceutically acceptable salt thereof wherein:

A is Sulfur;

X, Y, and Z, are each independently hydrogen, straight or branched alkyl of from 1 to 6 carbon atoms, cycloalkyl of from 3 to 8 carbon atoms, alkoxy, phenyl, benzyl, or halogen; and n is an integer of from 1 to 4.

2. A compound according to claim 1 and selected from:

3-Aminomethyl-4-thiophen-2-yl-butyric acid and

3-Aminomethyl-4-thiophen-3-yl-butyric acid.

3. A pharmaceutical composition comprising a therapeutically effective amount of a compound according to claim 1 and a pharmaceutically acceptable carrier.

* * * * *